United States Patent
Loo et al.

(10) Patent No.: US 9,995,753 B2
(45) Date of Patent: Jun. 12, 2018

(54) ANTI-PEMBROLIZUMAB ANTIBODIES

(71) Applicant: Merck Sharp & Dohme Corp., Rahway, NJ (US)

(72) Inventors: LiNa Loo, Monroe, NJ (US); Shuangping Shi, Mountain Lakes, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/274,330

(22) Filed: Sep. 23, 2016

(65) Prior Publication Data

US 2017/0089914 A1 Mar. 30, 2017

Related U.S. Application Data

(60) Provisional application No. 62/232,871, filed on Sep. 25, 2015.

(51) Int. Cl.
*C07K 16/28* (2006.01)
*G01N 33/68* (2006.01)
*C07K 16/42* (2006.01)
*G01N 33/94* (2006.01)

(52) U.S. Cl.
CPC ....... *G01N 33/686* (2013.01); *C07K 16/4266* (2013.01); *G01N 33/94* (2013.01); *C07K 2317/24* (2013.01); *C07K 2317/51* (2013.01); *C07K 2317/515* (2013.01); *C07K 2317/565* (2013.01); *G01N 2800/52* (2013.01)

(58) Field of Classification Search
CPC ............ C07K 2317/24; C07K 16/4266; C07K 2317/51; C07K 2317/76; C07K 2317/92; C07K 2317/565; C07K 2317/515; G01N 2800/52; G01N 33/686; G01N 33/94
See application file for complete search history.

(56) References Cited

U.S. PATENT DOCUMENTS

| 8,354,509 B2 | 1/2013 | Carven et al. |
| 8,900,587 B2 | 12/2014 | Carven et al. |
| 8,952,136 B2 | 2/2015 | Carven et al. |

FOREIGN PATENT DOCUMENTS

WO 2008156712 12/2008

OTHER PUBLICATIONS

Clinical Pharmacology and Biopharmaceutics reviews (2014 retrieved from https://www.accessdata.fda.gov/drugsatfda_docs/nda/2014/125514Orig1s000ClinPharmR.pdf).*

* cited by examiner

*Primary Examiner* — Tracy Vivlemore
*Assistant Examiner* — Carmencita M Belei
(74) *Attorney, Agent, or Firm* — Alysia A. Finnegan; Gloria M. Fuentes

(57) ABSTRACT

The present invention provides antibodies and antigen-binding fragments thereof that bind to the antibody pembrolizumab (pembrolizumab). These antibodies are useful, for example, for use as positive controls in assays for detecting the presence of anti-drug antibodies in a sample, e.g., the blood of a patient who has been administered pembrolizumab.

6 Claims, 12 Drawing Sheets

FR1-CDR1-FR2-CDR2-FR3-CDR3-FR4

ELVMTQTPSSVSAAVGDTVTINCQASETVATLLAWYQQKPGQPPKLLIYGASNLESGVPSRF
RGSGSGTEFTLTISGMKAEDAATYYCQYGYISTGSNTFGAGTNVEIK

>A30514-VH

FR1-CDR1-FR2-CDR2-FR3-CDR3-FR4

QEQLVESGGRLVTPGTPLTLTCTASGFSLGSDFMSWVRQAPGKGLEWIGYIDPRSDIPYYAS
WAKGRFTISKTSTTVDLKITSPTTEDTATYFCARDLNAGYFNGIFYIWGPGTLVTVSS (b)

A30523

>A30523-VL

FR1-CDR1-FR2-CDR2-FR3-CDR3-FR4

ELDMTQTPSSTSEPVGGTVTINCQASQTISSYLSWYQQKPGHPPKLLIYDASDLASGVPSRFS
GSRSGTQFTLTISGVQCDDAATYYCLGVYDYRSDDGAAFGGGTELEIL

>A30523-VH

FR1-CDR1-FR2-CDR2-FR3-CDR3-FR4

QEQLVESGGRLVTPGTPLTLTCTASGFSLGSDFMSWVRQAPGKGLEWIGYIDPRSDIPYYAS
WAKGRFTISKTSTTVDLKITSPTTEDTATYFCARDLNAGYFNGIFYIWGPGTLVTVSS

FR1-CDR1-FR2-CDR2-FR3-CDR3-FR4

ELVMTQTPSSVSAAVGGTVTITC<u>QASQSLSNLLA</u>WYQQKPGQPPKLLIY<u>GASNLES</u>GVPSRF
RGSGSGTDFTLTISGMKAEDAATYYC<u>QGGHYSGL</u>TFGNGTNVEIK

>A30633-VH

FR1-CDR1-FR2-CDR2-FR3-CDR3-FR4

QSLEESGGRLVTPGTPLTLTCTVSGFSLS<u>TNDMN</u>WVRQAPGKGLEWIG<u>VIYSDDTPDYATW</u>
AKGRFTISRTSTTVDLKITSPTTEDTATYFCAR<u>GHYDSAVYAYALNI</u>WGPGTLVTVSS

SEQUENCE LISTING

```
<160> NUMBER OF SEQ ID NOS: 35

<210> SEQ ID NO 1
<211> LENGTH: 327
<212> TYPE: DNA
<213> ORGANISM: Oryctolagus cuniculus

<400> SEQUENCE: 1
gagctcgtga tgacccagac tccatcctct gtgtctgcag ctgtgggaga cacagtcacc     60
atcaattgcc aggccagtga gactgttgcc accctcttag cctggtatca gcagaaacca    120
gggcagcctc ccaagctcct catttatggt gcatccaatc tggaatctgg ggtcccatcg    180
cgtttccgtg gcagtggatc tgggacagag ttcactctca ccatcagtgg catgaaggct    240
gaagatgctg ccacttatta ctgtcaatat ggttatatta gtactggatc taatactttc    300
ggtgcgggca ccaatgtgga aatcaaa                                        327

<210> SEQ ID NO 2
<211> LENGTH: 360
<212> TYPE: DNA
<213> ORGANISM: Orytolagus cuniculus

<400> SEQUENCE: 2
```

```
caggagcagc tggtggagtc cggaggtcgc ctggtcacgc ctgggacacc cctgacactc      60
acctgcacag cctctggatt ctccctcggt agcgacttca tgagctgggt ccgccaggct     120
ccagggaagg ggctggagtg gatcggatac attgatcctc gtagtgatat tccatattac     180
gcgagctggg cgaaaggccg attcaccatc tccaaaacct cgaccacggt ggatctgaaa     240
atcaccagtc cgacaaccga ggacacggcc acctatttct gtgccagaga tttaaatgct     300
ggttatttta atggtatatt ttatatttgg ggcccaggca ccctggtcac cgtctcttca     360
```

<210> SEQ ID NO 3
<211> LENGTH: 333
<212> TYPE: DNA
<213> ORGANISM: Orytolagus cuniculus

<400> SEQUENCE: 3

```
gagctcgata tgacccagac tccatcctcc acgtctgaac cagtgggagg cacagtcacc      60
atcaattgcc aggccagtca gaccattagt agctacttat cctggtatca gcagaaacca     120
gggcatcctc ccaagctcct gatctatgat gcatccgatc tggcatctgg ggtcccatcg     180
cgcttcagtg gcagcagatc tgggacacag ttcactctca ccatcagcgg cgtgcagtgt     240
gacgatgctg caacttacta ctgtctaggt gtttatgatt atagaagtga tgatggtgct     300
gctttcggcg agggaccga gctggagatc cta                                    333
```

<210> SEQ ID NO 4
<211> LENGTH: 360
<212> TYPE: DNA
<213> ORGANISM: Orytolagus cuniculus

<400> SEQUENCE: 4

```
caggagcagc tggtggagtc cggaggtcgc ctggtcacgc ctgggacacc cctgacactc      60
acctgcacag cctctggatt ctccctcggt agcgacttca tgagctgggt ccgccaggct     120
ccagggaagg ggctggaatg gatcggatac attgatcctc gtagtgatat tccatattac     180
gcgagctggg cgaaaggccg attcaccatc tccaaaacct cgaccacggt ggatctgaaa     240
atcaccagtc cgacaaccga ggacacggcc acctatttct gtgccagaga tttaaatgct     300
ggttatttta atggtatatt ttatatttgg ggcccaggca ccctggtcac cgtctcttca     360
```

<210> SEQ ID NO 5
<211> LENGTH: 321
<212> TYPE: DNA
<213> ORGANISM: Orytolagus cuniculus

<400> SEQUENCE: 5

```
gagctcgtga tgacccagac tccatcctct gtgtctgcag ctgtgggagg cacagtcacc      60
atcacttgcc aggccagtca gagtcttagc aacctcttag cctggtatca gcagaaacca     120
gggcagcctc ccaagctcct gatctatggt gcatccaatc tggaatctgg ggtcccatcg     180
cgtttccgtg gcagtggatc tgggacagac ttcactctca ccatcagtgg catgaaggct     240
gaagatgctg ccacttatta ctgtcaaggt ggtcattata gtggtttgac ttttggaaat     300
ggcaccaatg tggaaatcaa a                                                321
```

<210> SEQ ID NO 6
<211> LENGTH: 357
<212> TYPE: DNA
<213> ORGANISM: Orytolagus cuniculus

<400> SEQUENCE: 6

```
cagtcgctgg aggagtccgg gggtcgcctg gtcacgcctg ggacacccct gacactcacc    60
tgcacagtct ctggattctc cctcagtacc aacgacatga actgggtccg ccaggctcca   120
gggaaggggc tggaatggat cggagtcatt tatagtgatg ataccccga ctacgcgacc   180
tgggcgaaag gccgattcac catctccaga acctcgacca cggtggatct gaaaatcacc   240
agtccgacaa ccgaggacac ggccacctat ttctgtgcca gaggtcatta cgacagtgct   300
gtttatgctt atgcccttaa catctggggc ccaggcaccc tggtcaccgt ctcttca     357
```

<210> SEQ ID NO 7
<211> LENGTH: 109
<212> TYPE: PRT
<213> ORGANISM: Orytolagus cuniculus

<400> SEQUENCE: 7

Glu Leu Val Met Thr Gln Thr Pro Ser Ser Val Ser Ala Ala Val Gly
1               5                   10                  15

Asp Thr Val Thr Ile Asn Cys Gln Ala Ser Glu Thr Val Ala Thr Leu
                20                  25                  30

Leu Ala Trp Tyr Gln Gln Lys Pro Gly Gln Pro Pro Lys Leu Leu Ile
            35                  40                  45

Tyr Gly Ala Ser Asn Leu Glu Ser Gly Val Pro Ser Arg Phe Arg Gly
        50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Tyr Gly Tyr Ile Ser Thr Gly
                85                  90                  95

Ser Asn Thr Phe Gly Ala Gly Thr Asn Val Glu Ile Lys
            100                 105

<210> SEQ ID NO 8
<211> LENGTH: 120
<212> TYPE: PRT
<213> ORGANISM: Orytolagus cuniculus

<400> SEQUENCE: 8

Gln Glu Gln Leu Val Glu Ser Gly Gly Arg Leu Val Thr Pro Gly Thr
1               5                   10                  15

Pro Leu Thr Leu Thr Cys Thr Ala Ser Gly Phe Ser Leu Gly Ser Asp
                20                  25                  30

Phe Met Ser Trp Val Arg Gln Ala Pro Gly Lys Gly Leu Glu Trp Ile
            35                  40                  45

Gly Tyr Ile Asp Pro Arg Ser Asp Ile Pro Tyr Tyr Ala Ser Trp Ala
        50                  55                  60

Lys Gly Arg Phe Thr Ile Ser Lys Thr Ser Thr Val Asp Leu Lys
65                  70                  75                  80

Ile Thr Ser Pro Thr Thr Glu Asp Thr Ala Tyr Phe Cys Ala Arg
                85                  90                  95

Asp Leu Asn Ala Gly Tyr Phe Asn Gly Ile Phe Tyr Ile Trp Gly Pro
            100                 105                 110

Gly Thr Leu Val Thr Val Ser Ser
        115                 120

<210> SEQ ID NO 9
<211> LENGTH: 111
<212> TYPE: PRT

<213> ORGANISM: Orytolagus cuniculus

<400> SEQUENCE: 9

Glu Leu Asp Met Thr Gln Thr Pro Ser Ser Thr Ser Glu Pro Val Gly
1               5                   10                  15

Gly Thr Val Thr Ile Asn Cys Gln Ala Ser Gln Thr Ile Ser Ser Tyr
            20                  25                  30

Leu Ser Trp Tyr Gln Gln Lys Pro Gly His Pro Pro Lys Leu Leu Ile
        35                  40                  45

Tyr Asp Ala Ser Asp Leu Ala Ser Gly Val Pro Ser Arg Phe Ser Gly
    50                  55                  60

Ser Arg Ser Gly Thr Gln Phe Thr Leu Thr Ile Ser Gly Val Gln Cys
65                  70                  75                  80

Asp Asp Ala Ala Thr Tyr Tyr Cys Leu Gly Val Tyr Asp Tyr Arg Ser
                85                  90                  95

Asp Asp Gly Ala Ala Phe Gly Gly Gly Thr Glu Leu Glu Ile Leu
            100                 105                 110

<210> SEQ ID NO 10
<211> LENGTH: 120
<212> TYPE: PRT
<213> ORGANISM: Orytolagus cuniculus

<400> SEQUENCE: 10

Gln Glu Gln Leu Val Glu Ser Gly Gly Arg Leu Val Thr Pro Gly Thr
1               5                   10                  15

Pro Leu Thr Leu Thr Cys Thr Ala Ser Gly Phe Ser Leu Gly Ser Asp
            20                  25                  30

Phe Met Ser Trp Val Arg Gln Ala Pro Gly Lys Gly Leu Glu Trp Ile
        35                  40                  45

Gly Tyr Ile Asp Pro Arg Ser Asp Ile Pro Tyr Tyr Ala Ser Trp Ala
    50                  55                  60

Lys Gly Arg Phe Thr Ile Ser Lys Thr Ser Thr Thr Val Asp Leu Lys
65                  70                  75                  80

Ile Thr Ser Pro Thr Thr Glu Asp Thr Ala Thr Tyr Phe Cys Ala Arg
                85                  90                  95

Asp Leu Asn Ala Gly Tyr Phe Asn Gly Ile Phe Tyr Ile Trp Gly Pro
            100                 105                 110

Gly Thr Leu Val Thr Val Ser Ser
        115                 120

<210> SEQ ID NO 11
<211> LENGTH: 107
<212> TYPE: PRT
<213> ORGANISM: Orytolagus cuniculus

<400> SEQUENCE: 11

Glu Leu Val Met Thr Gln Thr Pro Ser Ser Val Ser Ala Ala Val Gly
1               5                   10                  15

Gly Thr Val Thr Ile Thr Cys Gln Ala Ser Gln Ser Leu Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Asp Phe Thr Leu Thr Ile Ser Gly Met Lys Ala
65                  70                  75                  80

Glu Asp Ala Ala Thr Tyr Tyr Cys Gln Gly Gly His Tyr Ser Gly Leu
            85                  90                  95

Thr Phe Gly Asn Gly Thr Asn Val Glu Ile Lys
            100                 105

<210> SEQ ID NO 12
<211> LENGTH: 119
<212> TYPE: PRT
<213> ORGANISM: Orytolagus cuniculus

<400> SEQUENCE: 12

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Asn Asp
            20                  25                  30

Met Asn Trp Val Arg Gln Ala Pro Gly Lys Gly Leu Glu Trp Ile Gly
        35                  40                  45

Val Ile Tyr Ser Asp Asp Thr Pro Asp Tyr Ala Thr Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Glu Asp Thr Ala Thr Tyr Phe Cys Ala Arg Gly His
                85                  90                  95

Tyr Asp Ser Ala Val Tyr Ala Tyr Ala Leu Asn Ile Trp Gly Pro Gly
            100                 105                 110

Thr Leu Val Thr Val Ser Ser
        115

<210> SEQ ID NO 13
<211> LENGTH: 11
<212> TYPE: PRT
<213> ORGANISM: Orytolagus cuniculus

<400> SEQUENCE: 13

Gln Ala Ser Glu Thr Val Ala Thr Leu Leu Ala
1               5                   10

<210> SEQ ID NO 14
<211> LENGTH: 7
<212> TYPE: PRT
<213> ORGANISM: Orytolagus cuniculus

<400> SEQUENCE: 14

Gly Ala Ser Asn Leu Glu Ser
1               5

<210> SEQ ID NO 15
<211> LENGTH: 12
<212> TYPE: PRT
<213> ORGANISM: Orytolagus cuniculus

<400> SEQUENCE: 15

Gln Tyr Gly Tyr Ile Ser Thr Gly Ser Asn Thr Phe
1               5                   10

<210> SEQ ID NO 16
<211> LENGTH: 5
<212> TYPE: PRT
<213> ORGANISM: Orytolagus cuniculus

<400> SEQUENCE: 16

-continued

Ser Asp Phe Met Ser
1               5

<210> SEQ ID NO 17
<211> LENGTH: 17
<212> TYPE: PRT
<213> ORGANISM: Orytolagus cuniculus

<400> SEQUENCE: 17

Tyr Ile Asp Pro Arg Ser Asp Ile Pro Tyr Tyr Ala Ser Trp Ala Lys
1               5                   10                  15
Gly

<210> SEQ ID NO 18
<211> LENGTH: 13
<212> TYPE: PRT
<213> ORGANISM: Orytolagus cuniculus

<400> SEQUENCE: 18

Asp Leu Asn Ala Gly Tyr Phe Asn Gly Ile Phe Tyr Ile
1               5                   10

<210> SEQ ID NO 19
<211> LENGTH: 11
<212> TYPE: PRT
<213> ORGANISM: Orytolagus cuniculus

<400> SEQUENCE: 19

Gln Ala Ser Gln Thr Ile Ser Ser Tyr Leu Ser
1               5                   10

<210> SEQ ID NO 20
<211> LENGTH: 7
<212> TYPE: PRT
<213> ORGANISM: Orytolagus cuniculus

<400> SEQUENCE: 20

Asp Ala Ser Asp Leu Ala Ser
1               5

<210> SEQ ID NO 21
<211> LENGTH: 13
<212> TYPE: PRT
<213> ORGANISM: Orytolagus cuniculus

<400> SEQUENCE: 21

Leu Gly Val Tyr Asp Tyr Arg Ser Asp Asp Gly Ala Ala
1               5                   10

<210> SEQ ID NO 22
<211> LENGTH: 5
<212> TYPE: PRT
<213> ORGANISM: Orytolagus cuniculus

<400> SEQUENCE: 22

Ser Asp Phe Met Ser
1               5

<210> SEQ ID NO 23
<211> LENGTH: 17
<212> TYPE: PRT
<213> ORGANISM: Orytolagus cuniculus

<400> SEQUENCE: 23

-continued

```
Tyr Ile Asp Pro Arg Ser Asp Ile Pro Tyr Tyr Ala Ser Trp Ala Lys
1               5                   10                  15

Gly

<210> SEQ ID NO 24
<211> LENGTH: 13
<212> TYPE: PRT
<213> ORGANISM: Orytolagus cuniculus

<400> SEQUENCE: 24

Asp Leu Asn Ala Gly Tyr Phe Asn Gly Ile Phe Tyr Ile
1               5                   10

<210> SEQ ID NO 25
<211> LENGTH: 11
<212> TYPE: PRT
<213> ORGANISM: Orytolagus cuniculus

<400> SEQUENCE: 25

Gln Ala Ser Gln Ser Leu Ser Asn Leu Leu Ala
1               5                   10

<210> SEQ ID NO 26
<211> LENGTH: 7
<212> TYPE: PRT
<213> ORGANISM: Orytolagus cuniculus

<400> SEQUENCE: 26

Gly Ala Ser Asn Leu Glu Ser
1               5

<210> SEQ ID NO 27
<211> LENGTH: 9
<212> TYPE: PRT
<213> ORGANISM: Orytolagus cuniculus

<400> SEQUENCE: 27

Gln Gly Gly His Tyr Ser Gly Leu Thr
1               5

<210> SEQ ID NO 28
<211> LENGTH: 5
<212> TYPE: PRT
<213> ORGANISM: Orytolagus cuniculus

<400> SEQUENCE: 28

Thr Asn Asp Met Asn
1               5

<210> SEQ ID NO 29
<211> LENGTH: 16
<212> TYPE: PRT
<213> ORGANISM: Orytolagus cuniculus

<400> SEQUENCE: 29

Val Ile Tyr Ser Asp Asp Thr Pro Asp Tyr Ala Thr Trp Ala Lys Gly
1               5                   10                  15

<210> SEQ ID NO 30
<211> LENGTH: 14
<212> TYPE: PRT
<213> ORGANISM: Orytolagus cuniculus

<400> SEQUENCE: 30
```

```
Gly His Tyr Asp Ser Ala Val Tyr Ala Tyr Ala Leu Asn Ile
1               5                   10
```

```
<210> SEQ ID NO 31
<211> LENGTH: 547
<212> TYPE: PRT
<213> ORGANISM: Artificial Sequence
<220> FEATURE:
<223> OTHER INFORMATION: Homo sapiens; Orytolagus cuniculus

<400> SEQUENCE: 31

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Asn Asp
                20                  25                  30

Met Asn Trp Val Arg Gln Ala Pro Gly Lys Gly Leu Glu Trp Ile Gly
            35                  40                  45

Val Ile Tyr Ser Asp Asp Thr Pro Asp Tyr Ala Thr Trp Ala Lys Gly
        50                  55                  60

Arg Phe Thr Ile Ser Arg Thr Ser Thr Thr Val Asp Leu Lys Ile Thr
65                  70                  75                  80

Ser Pro Thr Thr Glu Asp Thr Ala Thr Tyr Phe Cys Ala Arg Gly His
                85                  90                  95

Tyr Asp Ser Ala Val Tyr Ala Tyr Ala Leu Asn Ile Trp Gly Pro Gly
            100                 105                 110

Thr Leu Val Thr Val Ser Ser Ala Ser Thr Gln Ser Pro Ser Val Phe
        115                 120                 125

Pro Leu Thr Arg Cys Cys Lys Asn Ile Pro Ser Asn Ala Thr Ser Val
130                 135                 140

Thr Leu Gly Cys Leu Ala Thr Gly Tyr Phe Pro Glu Pro Val Met Val
145                 150                 155                 160

Thr Trp Asp Thr Gly Ser Leu Asn Gly Thr Thr Met Thr Leu Pro Ala
                165                 170                 175

Thr Thr Leu Thr Leu Ser Gly His Tyr Ala Thr Ile Ser Leu Leu Thr
            180                 185                 190

Val Ser Gly Ala Trp Ala Lys Gln Met Phe Thr Cys Arg Val Ala His
        195                 200                 205

Thr Pro Ser Ser Thr Asp Trp Val Asp Asn Lys Thr Phe Ser Val Cys
210                 215                 220

Ser Arg Asp Phe Thr Pro Pro Thr Val Lys Ile Leu Gln Ser Ser Cys
225                 230                 235                 240

Asp Gly Gly Gly His Phe Pro Pro Thr Ile Gln Leu Leu Cys Leu Val
                245                 250                 255

Ser Gly Tyr Thr Pro Gly Thr Ile Asn Ile Thr Trp Leu Glu Asp Gly
            260                 265                 270

Gln Val Met Asp Val Asp Leu Ser Thr Ala Ser Thr Thr Gln Glu Gly
        275                 280                 285

Glu Leu Ala Ser Thr Gln Ser Glu Leu Thr Leu Ser Gln Lys His Trp
290                 295                 300

Leu Ser Asp Arg Thr Tyr Thr Cys Gln Val Thr Tyr Gln Gly His Thr
305                 310                 315                 320

Phe Glu Asp Ser Thr Lys Lys Cys Ala Asp Ser Asn Pro Arg Gly Val
                325                 330                 335

Ser Ala Tyr Leu Ser Arg Pro Ser Pro Phe Asp Leu Phe Ile Arg Lys
            340                 345                 350
```

Ser Pro Thr Ile Thr Cys Leu Val Val Asp Leu Ala Pro Ser Lys Gly
        355                 360                 365

Thr Val Asn Leu Thr Trp Ser Arg Ala Ser Gly Lys Pro Val Asn His
    370                 375                 380

Ser Thr Arg Lys Glu Glu Lys Gln Arg Asn Gly Thr Leu Thr Val Thr
385                 390                 395                 400

Ser Thr Leu Pro Val Gly Thr Arg Asp Trp Ile Glu Gly Glu Thr Tyr
                405                 410                 415

Gln Cys Arg Val Thr His Pro His Leu Pro Arg Ala Leu Met Arg Ser
                420                 425                 430

Thr Thr Lys Thr Ser Gly Pro Arg Ala Ala Pro Glu Val Tyr Ala Phe
            435                 440                 445

Ala Thr Pro Glu Trp Pro Gly Ser Arg Asp Lys Arg Thr Leu Ala Cys
    450                 455                 460

Leu Ile Gln Asn Phe Met Pro Glu Asp Ile Ser Val Gln Trp Leu His
465                 470                 475                 480

Asn Glu Val Gln Leu Pro Asp Ala Arg His Ser Thr Thr Gln Pro Arg
                485                 490                 495

Lys Thr Lys Gly Ser Gly Phe Phe Val Phe Ser Arg Leu Glu Val Thr
                500                 505                 510

Arg Ala Glu Trp Glu Gln Lys Asp Glu Phe Ile Cys Arg Ala Val His
            515                 520                 525

Glu Ala Ala Ser Pro Ser Gln Thr Val Gln Arg Ala Val Ser Val Asn
        530                 535                 540

Pro Gly Lys
545

<210> SEQ ID NO 32
<211> LENGTH: 1644
<212> TYPE: DNA
<213> ORGANISM: Artificial Sequence
<220> FEATURE:
<223> OTHER INFORMATION: Homo sapiens; Orytolagus cuniculus

<400> SEQUENCE: 32
cagagcctgg aagagagcgg cggcagactg gtgaccctg gcacacccct caccctgaca      60
tgtacagtgt ccggctttag cctgagcacc aacgacatga attgggtgag acaggccct     120 ggcaaaggac tcgagtggat cggcgtgatt tacagcgacg acacaccga ctacgccaca     180 tgggccaagg gaagattcac catcagcagg accagcacca ccgtggacct gaaaatcaca     240 tccctacca ccgaagacac cgccacctac ttctgcgcca ggggccacta cgatagcgcc      300
gtctacgcct acgccctcaa tatttggggc cctggcacac tggtgaccgt gagcagcgcc     360
agcacccaaa gccccagcgt gttcccctg acaaggtgtt gcaagaacat ccccagcaac     420
gccaccagcg tcacactggg atgcctggcc accggctact cccccgaacc cgtcatggtg     480
acctgggata ccggcagcct gaatggcacc acaatgaccc tccccgccac aaccctgaca     540
ctgagcggcc actacgccac catcagcctg ctgaccgtgt ccggcgcctg gccaaacag      600 atgttcacct gcagagtggc ccacacccc agctccacag actgggtgga caacaagacc     660
ttcagcgtgt gctccaggga ctttacaccc ctaccgtga agatcctgca gtccagctgt     720
gatggcggcg ccacttccc tcctaccatt cagctcctgt gcctggtgag cggctacaca     780
cccggcacca tcaacatcac ctggctggag gatggacagg tgatggacgt ggacctcagc     840
acagcctcca ccacacagga gggagagctg gccagcaccc agtccgagct caccctgagc     900

```
cagaagcact ggctgtccga caggacctat acatgccagg tcacctacca gggccacacc    960
ttcgaggact ccacaaagaa gtgcgccgac agcaatccca gaggcgtctc cgcctacctg   1020
tccaggccta gccccttcga tctgttcatc aggaagagcc ccaccattac atgcctggtg   1080
gtggacctgg ccccctccaa gggcaccgtg aacctgacct ggagcagagc cagcggcaag   1140
cccgtcaacc actccaccag aaaggaggag aagcagagaa acggcaccct gacagtgacc   1200
tccacactcc ctgtgggaac cagggactgg atcgagggcg agacctatca gtgcagagtc   1260
acccatcccc atctgcccag agccctgatg agaagcacca ccaagacatc cggccccaga   1320
gctgctcctg aggtgtacgc ctttgctacc cctgagtggc ccggctccag ggataagagg   1380
accctcgctt gcctgatcca gaacttcatg cccgaagaca tcagcgtgca gtggctgcac   1440
aacgaggtgc agctgcctga cgccaggcac agcacaaccc agcctaggaa gaccaaaggc   1500
tccggctttt tcgtgttctc caggctcgag gtgaccaggg ccgagtggga gcagaaagat   1560
gagttcatct gcagggccgt gcacgaagct gctagcccta ccagaccgt gcaagggct   1620 gtgtccgtca accccggcaa gtga                                         1644
```

<210> SEQ ID NO 33
<211> LENGTH: 214
<212> TYPE: PRT
<213> ORGANISM: Artificial Sequence
<220> FEATURE:
<223> OTHER INFORMATION: Homo sapiens; Orytolagus cuniculus

<400> SEQUENCE: 33

```
Glu Leu Val Met Thr Gln Thr Pro Ser Ser Val Ser Ala Ala Val Gly
1               5                   10                  15

Gly Thr Val Thr Ile Thr Cys Gln Ala Ser Gln Ser Leu Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Asp Phe Thr Leu Thr Ile Ser Gly Met Lys Ala
65                  70                  75                  80

Glu Asp Ala Ala Thr Tyr Tyr Cys Gln Gly Gly His Tyr Ser Gly Leu
                85                  90                  95

Thr Phe Gly Asn Gly Thr Asn Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 34
<211> LENGTH: 645
<212> TYPE: DNA
<213> ORGANISM: Artificial Sequence
<220> FEATURE:
<223> OTHER INFORMATION: Homo sapiens; Orytolagus cuniculus

<400> SEQUENCE: 34

```
gagctggtga tgacccagac accctcctcc gtgagcgctg ctgtgggcgg aaccgtgacc      60
atcacctgcc aagccagcca gtccctgtcc aacctgctgg cctggtacca gcagaagcct     120
ggccagcccc ccaaactgct gatctacggc gccagcaacc tggagagcgg cgtgcctagc     180
aggttcaggg gaagcggcag cggcaccgac ttcaccctga ccatcagcgg catgaaggcc     240
gaggatgccg ccacctacta ctgtcagggc ggccactaca gcggcctgac cttcggcaac     300
ggcaccaacg tcgagatcaa gaggaccgtg gccgctccca gcgtctttat tttcccccct     360
tccgacgagc aactgaaaag cggcaccgcc agcgtggtgt gcctgctgaa caacttctac     420
cccagggagg ccaaggtgca gtggaaggtg gataacgccc tgcaaagcgg caatagccag     480
gagagcgtga ccgagcagga ctccaaggac agcacctact ccctgagctc cacactgaca     540
ctgagcaagg ccgactacga aagcacaag gtgtatgcct gcgaggtgac ccaccagggc     600
ctgagctccc ctgtgaccaa gagcttcaac agaggagagt gctga                    645
```

<210> SEQ ID NO 35
<211> LENGTH: 428
<212> TYPE: PRT
<213> ORGANISM: Homo sapiens

<400> SEQUENCE: 35

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

-continued

```
Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225             230                 235                 240

Val Val Asp Leu Ala Pro Ser Lys Gly Thr Val Asn Leu Thr Trp Ser
            245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
            275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
            325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
    370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
            405                 410                 415

Thr Val Gln Arg Ala Val Ser Val Asn Pro Gly Lys
            420                 425
```

ANTI-PEMBROLIZUMAB ANTIBODIES

This Application claims the benefit of U.S. Provisional Patent Application No. 62/232,871, filed Sep. 25, 2015; which is herein incorporated by reference in its entirety.

FIELD OF THE INVENTION

The field of the present invention relates to antibodies that bind to pembrolizumab and methods of using such antibodies, for example, for detecting the presence of anti-drug antibodies in a sample.

BACKGROUND OF THE INVENTION

The possibility exists that some therapeutic proteins, such as antibodies, have immunogenic potential, and administration of the therapeutic proteins to a patient sometimes results in the production of antibodies against the therapeutic protein. Such anti-drug antibodies (ADA) may reduce the effectiveness of the therapeutic protein; for example, they may bind to or/and neutralize the therapeutic protein, resulting in changes of drug pharmacokinetics or pharmacodynamics that alters drug efficacy. ADA may cause serious side effects, including allergic reactions, cross-reactivity against endogenous proteins, and complement activation. A life-threatening deficiency syndrome can result if ADA cross-reacts with and neutralizes a critical endogenous protein. Thus, assays and reagents for determining the presence of ADAs in a sample for a patient who has received an antibody therapy, such as pembrolizumab, is of great interest.

SUMMARY OF THE INVENTION

The present invention provides an antibody or antigen-binding fragment thereof (e.g., an antibody) that binds pembrolizumab wherein the antibody or antigen-binding fragment thereof comprises: (a) the CDR1, CDR2, and CDR3 of a $V_L$ domain of an immunoglobulin chain that comprises the amino acid sequence set forth in 7, 9 or 11; and/or (b) the CDR1, CDR2, and CDR3 of a $V_H$ domain of an immunoglobulin chain that comprises the amino acid sequence set forth in SEQ ID NO: 8, 10 or 12. In an embodiment of the invention, the antibody or fragment is an antibody comprising: (1) a light chain variable domain comprising: CDR-L1 that comprises the amino acid sequence: QASETVATLLA (SEQ ID NO: 13); CDR-L2 that comprises the amino acid sequence: GASNLES (SEQ ID NO: 14); and CDR-L3 that comprises the amino acid sequence: QYGYISTGSNT (SEQ ID NO: 15); and/or a heavy chain variable domain comprising: CDR-H1 that comprises the amino acid sequence: SDFMS (SEQ ID NO: 16); CDR-H2 that comprises the amino acid sequence: YIDPRSDIPYYASWAKG (SEQ ID NO: 17); and CDR-H3 that comprises the amino acid sequence: DLNAGYFNGI-FYI (SEQ ID NO: 18); (2) a light chain variable domain comprising: CDR-L1 that comprises the amino acid sequence: QASQTISSYLS (SEQ ID NO: 19); CDR-L2 that comprises the amino acid sequence: DASDLAS (SEQ ID NO: 20); and CDR-L3 that comprises the amino acid sequence: LGVYDYRSDDGAA (SEQ ID NO: 21); and/or a heavy chain variable domain comprising: CDR-H1 that comprises the amino acid sequence: SDFMS (SEQ ID NO: 22); CDR-H2 that comprises the amino acid sequence: YIDPRSDIPYYASWAKG (SEQ ID NO: 23); and CDR-H3 that comprises the amino acid sequence: DLNAGYFNGI-FYI (SEQ ID NO: 24); or (3) a light chain variable domain comprising: CDR-L1 that comprises the amino acid sequence: QASQSLSNLLA (SEQ ID NO: 25); CDR-L2 that comprises the amino acid sequence: GASNLES (SEQ ID NO: 26); and CDR-L3 that comprises the amino acid sequence: QGGHYSGLT (SEQ ID NO: 27); and/or a heavy chain variable domain comprising: CDR-H1 that comprises the amino acid sequence: TNDMN (SEQ ID NO: 28); CDR-H2 that comprises the amino acid sequence: VIYSD-DTPDYATWAKG (SEQ ID NO: 29); and CDR-H3 that comprises the amino acid sequence: GHYDSAVYAYALNI (SEQ ID NO: 30).

The present invention provides an antibody or antigen-binding fragment thereof (e.g., an antibody) that binds pembrolizumab wherein the antibody or antigen-binding fragment thereof comprises a light chain immunoglobulin, a heavy chain immunoglobulin, or both a light and heavy chain immunoglobulin, selected from the group consisting of: (1) a light chain immunoglobulin comprising an amino acid sequence having at least 90% (e.g., 95%, 96%, 97%, 98%, 99% or 100%) amino acid sequence identity to the amino acid sequence set forth in SEQ ID NO: 7, and/or a heavy chain immunoglobulin comprising an amino acid sequence having at least 90% (e.g., 95%, 96%, 97%, 98%, 99% or 100%) amino acid sequence identity to the amino acid sequence set forth in SEQ ID NO: 8; (2) a light chain immunoglobulin comprising an amino acid sequence having at least 90% amino acid sequence identity to the amino acid sequence set forth in SEQ ID NO: 9, and/or a heavy chain immunoglobulin comprising an amino acid sequence having at least 90% (e.g., 95%, 96%, 97%, 98%, 99% or 100%) amino acid sequence identity to the amino acid sequence set forth in SEQ ID NO: 10; (3) a light chain immunoglobulin comprising an amino acid sequence having at least 90% (e.g., 95%, 96%, 97%, 98%, 99% or 100%) amino acid sequence identity to the amino acid sequence set forth in SEQ ID NO: 11, and/or a heavy chain immunoglobulin comprising an amino acid sequence having at least 90% (e.g., 95%, 96%, 97%, 98%, 99% or 100%) amino acid sequence identity to the amino acid sequence set forth in SEQ ID NO: 12. In an embodiment of the invention, the antibody or antigen-binding fragment comprises (1) a light chain immunoglobulin comprising CDR-L1, CDR-L2 and CDR-L3 of the immunoglobulin comprising the amino acid sequence of SEQ ID NO: 7, and having at least 90% (e.g., 95%, 96%, 97%, 98%, 99% or 100%) amino acid sequence identity to the amino acid sequence set forth in SEQ ID NO: 7, and/or a heavy chain immunoglobulin comprising CDR-H1, CDR-H2 and CDR-H3 of the immunoglobulin comprising the amino acid sequence of SEQ ID NO: 8, and having at least 90% (e.g., 95%, 96%, 97%, 98%, 99% or 100%) amino acid sequence identity to the amino acid sequence set forth in SEQ ID NO: 8; (2) a light chain immunoglobulin comprising CDR-L1, CDR-L2 and CDR-L3 of the immunoglobulin comprising the amino acid sequence of SEQ ID NO: 9, and having at least 90% (e.g., 95%, 96%, 97%, 98%, 99% or 100%) amino acid sequence identity to the amino acid sequence set forth in SEQ ID NO: 9, and/or a heavy chain immunoglobulin comprising CDR-H1, CDR-H2 and CDR-H3 of the immunoglobulin comprising the amino acid sequence of SEQ ID NO: 10, and having at least 90% (e.g., 95%, 96%, 97%, 98%, 99% or 100%) amino acid sequence identity to the amino acid sequence set forth in SEQ ID NO: 10; (3) a light chain immunoglobulin comprising CDR-L1, CDR-L2 and CDR-L3 of the immunoglobulin comprising the amino acid sequence of SEQ ID NO: 11, and having at least 90% (e.g., 95%, 96%, 97%, 98%, 99% or 100%) amino acid sequence identity to the amino acid sequence set forth in SEQ ID NO: 11, and/or a heavy chain immunoglobulin comprising CDR-H1, CDR-H2 and CDR-H3 of the immunoglobulin comprising the amino acid sequence of SEQ ID NO: 12, and having at least 90% (e.g., 95%, 96%, 97%, 98%, 99% or 100%) amino acid sequence identity to the amino acid sequence set forth in SEQ ID NO: 12. In an embodiment of the invention, the antibody or antigen-binding fragment comprises (1) a light chain immunoglobulin comprising the amino acid sequence set forth in SEQ ID NO: 7, and/or a heavy chain immunoglobulin comprising the amino acid sequence set forth in SEQ ID NO: 8; or (2) a light chain immunoglobulin comprising the amino acid sequence set forth in SEQ ID NO: 9, and/or a heavy chain immunoglobulin comprising the amino acid sequence set forth in SEQ ID NO: 10; or (3) a light chain immunoglobulin comprising the amino acid sequence set forth in SEQ ID NO: 11, and/or a heavy chain immunoglobulin comprising the amino acid sequence set forth in SEQ ID NO: 12.

The present invention also provides an antibody or antigen-binding fragment thereof that cross-blocks any of the anti-pembrolizumab antibodies or antigen-binding fragments thereof of the present invention described herein from binding to pembrolizumab, for example, in an antibody cross-blocking assay.

The present invention includes a composition comprising an anti-pembrolizumab antibody or antigen-binding fragment thereof of the present invention complexed with pembrolizumab, and, optionally, a labeled secondary antibody or antigen-binding fragment bound to said anti-pembrolizumab antibody or fragment.

The present invention also encompasses a polypeptide comprising an amino acid sequence selected from the group consisting of SEQ ID NOs: 7-12 as well as polynucleotides encoding such polypeptides (e.g., SEQ ID NOs: 1-6) and vectors comprising any such polynucleotides and host cells (e.g., Chinese hamster ovary cell) comprising such vectors, polynucleotides and/or polypeptides.

The present invention also includes a method of producing an antibody or antigen-binding fragment thereof or immunoglobulin polypeptide set forth herein comprising: a. culturing a host cell (e.g., Chinese hamster ovary cell) comprising a polynucleotide encoding the polypeptide or an immunoglobulin chain of the antibody or antigen-binding fragment in a culture medium under conditions favorable to expression of the polynucleotide; and b. optionally, recovering the antibody, antigen-binding fragment or polypeptide from the host cell and/or culture medium. Any antibody or antigen-binding fragment thereof that binds human pembrolizumab or polypeptide which is the product of such a method forms part of the present invention.

The present invention also provides a method for making the composition complex between pembrolizumab and an anti-pembrolizumab antibody or antigen-binding fragment thereof of the present invention comprising contacting the anti-pembrolizumab antibody or antigen-binding fragment with pembrolizumab, and, optionally, contacting the anti-pembrolizumab antibody or fragment with a labeled secondary antibody or antigen-binding fragment.

In addition, the present invention provides a method for detecting anti-pembrolizumab antibodies and antigen-binding fragments in a sample comprising: (i) contacting pembrolizumab that is immobilized to a support with the sample; (ii) contacting any anti-pembrolizumab antibodies or antigen-binding fragments in the sample that are bound to the pembrolizumab with a labeled secondary antibody that binds to said anti-pembrolizumab antibodies or fragments; and (iii) determining the presence of label associated with the support; wherein the presence of the label associated with the support indicates the presence of anti-pembrolizumab antibodies and antigen-binding fragments in the sample; and (a) contacting pembrolizumab that is immobilized to a support with an anti-pembrolizumab antibody or antigen-binding fragment thereof of the present invention; (b) contacting anti-pembrolizumab antibody or fragment bound to the pembrolizumab with a labeled secondary antibody that binds to said anti-pembrolizumab antibody or fragment; and (c) determining the presence of label associated with the support; wherein the presence of the label associated with the support indicates that the assay is functioning correctly.

BRIEF DESCRIPTION OF THE FIGURES

FIG. 11 (a)-(c). (a) A30514 immunoglobulin sequences; (b) A30523 immunoglobulin sequences; (c) A30633 immunoglobulin sequences.

DETAILED DESCRIPTION OF THE INVENTION

Figure 1:
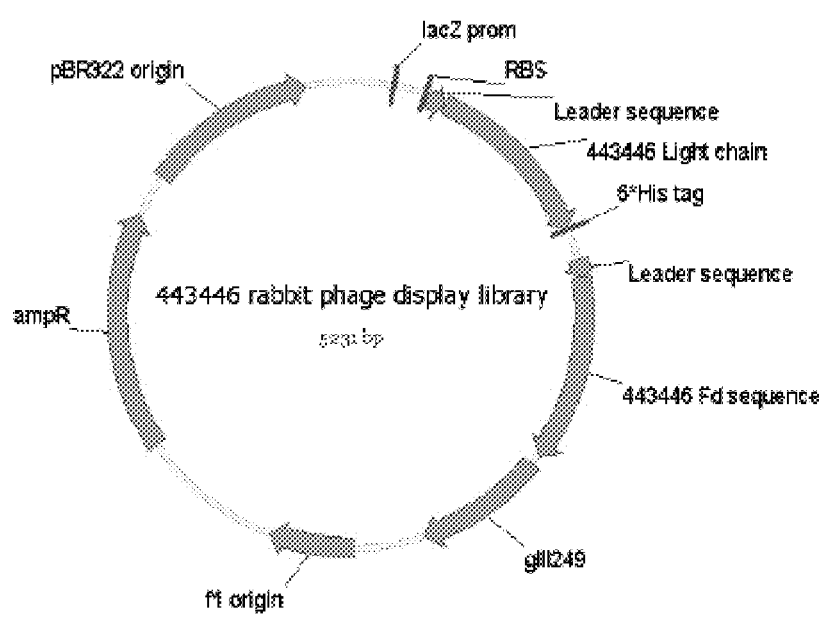
FIG. 1. Sketch map of 443446 rabbit phage display library.

The present invention provides antibodies which bind to the antibody pembrolizumab. Such antibodies are useful, for example, in methods for identifying whether a sample contains anti-drug antibodies that bind to pembrolizumab.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) Nature 342:877-883; Foote and Winter (1992) *J. Mol. Biol.* 224:487-499; U.S. Pat. No. 6,329,511).

Single chain antibodies and diabodies are described (see, e.g., Malecki et al. (2002) *Proc. Natl. Acad. Sci.* USA 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not always necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, or polyethylene glycol (PEG). Antibodies may be useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, $2^{nd}$ ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Antibodies

The present invention includes anti-pembrolizumab antibodies and antigen-binding fragments that bind to the anti-PD1 antibody pembrolizumab or an epitope thereof and methods of use thereof.

In an embodiment of the invention, the anti-pembrolizumab antibodies and antigen-binding fragments thereof of the present invention bind to pembrolizumab with a $K_D$ of about $10^{-7}$M or higher affinity (e.g., $10^{-9}$M, $10^{-10}$M, $10^{-11}$M, $10^{-12}$M). In an embodiment of the invention, the antibodies and antigen-binding fragments bind to pembrolizumab with a $K_{off}$ rate of about $1.2 \times 10^{-3}$/sec to about $6.5 \times 10^{-5}$/sec (e.g., $1.2 \times 10^{-3}$/sec, $3.4 \times 10^{-4}$/sec or $5 \times 10^{-5}$/sec).

An antibody or antigen-binding fragment thereof that binds to pembrolizumab or an epitope thereof may be referred to herein as "anti-pembrolizumab".

The present invention includes isolated anti-pembrolizumab antibodies and antigen-binding fragments thereof and methods of use thereof as well as polypeptide immunoglobulin chains thereof and polynucleotides encoding such polypeptides and isolated vectors including such polynucleotides.

The present invention includes isolated anti-pembrolizumab antibodies and antigen-binding fragments thereof (e.g., A30514, A30523 or A30633) and methods of use thereof as well as isolated polypeptide immunoglobulin chains thereof and isolated polynucleotides encoding such polypeptides and isolated vectors including such polynucleotides. "Isolated" antibodies or antigen-binding fragments thereof, polypeptides, polynucleotides and vectors, are at least partially free of other biological molecules from the cells or cell culture from which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The present invention also provides anti-pembrolizumab antibodies and antigen-binding fragments wherein the antibody or antigen-binding fragment thereof comprises one or more of the following immunoglobulin light chain variable domains and/or immunoglobulin heavy chain variable domains. Antibodies and fragments comprising one or more light chain CDRs (e.g., all three of CDR-L1, CDR-L2 and CDR-L3) and/or heavy chain CDRs (e.g., all three of CDR-H1, CDR-H2 and CDR-H3) are also part of the present invention.

The immunoglobulin chains of the present invention (e.g., A30514, A30523 and A30633) with the CDRs underscored as well as the nucleotide sequences of the polynucleotides of the present invention, which encode such immunoglobulin chains, are set forth below:

```
>A30514-VL
                                                        (SEQ ID NO: 1)
gagctcgtga tgacccagac tccatcctct gtgtctgcag ctgtgggaga cacagtcacc   60
atcaattgcc aggccagtga gactgttgcc accctcttag cctggtatca gcagaaacca  120
gggcagcctc ccaagctcct catttatggt gcatccaatc tggaatctgg ggtcccatcg  180
cgtttccgtg gcagtggatc tgggacagag ttcactctca ccatcagtgg catgaaggct  240
gaagatgctg ccacttatta ctgtcaatat ggttatatta gtactggatc taatactttc  300
ggtgcgggca ccaatgtgga aatcaaa                                      327

>A30514-VH
                                                        (SEQ ID NO: 2)
caggagcagc tggtggagtc cggaggtcgc ctggtcacgc ctgggacacc cctgacactc   60
acctgcacag cctctggatt ctccctcggt agcgacttca tgagctgggt ccgccaggct  120
ccagggaagg ggctggagtg gatcggatac attgatcctg gtagtgatat tccatattac  180
gcgagctggg cgaaaggccg attcaccatc tccaaaacct cgaccacggt ggatctgaaa  240
atcaccagtc cgacaaccga ggacacggcc acctatttct gtgccagaga tttaaatgct  300
ggttatttta atggtatatt ttatatttgg ggcccaggca ccctggtcac cgtctcttca  360

>A30523-VL
                                                        (SEQ ID NO: 3)
gagctcgata tgacccagac tccatcctcc acgtctgaac cagtgggagg cacagtcacc   60
atcaattgcc aggccagtca gaccattagt agctacttat cctggtatca gcagaaacca  120
gggcatcctc ccaagctcct gatctatgat gcatccgatc tggcatctgg ggtcccatcg  180
cgcttcagtg gcagcagatc tgggacacag ttcactctca ccatcagcgg cgtgcagtgt  240
gacgatgctg caacttacta ctgtctaggt gtttatgatt atagaagtga tgatggtgct  300
```

-continued

```
gctttcggcg agggaccga gctggagatc cta                          333
>A30523-VH
                                                    (SEQ ID NO: 4)
caggagcagc tggtggagtc cggaggtcgc ctggtcacgc ctgggacacc cctgacactc  60
acctgcacag cctctggatt ctccctcggt agcgacttca tgagctgggt ccgccaggct 120
ccagggaagg ggctggaatg gatcggatac attgatcctc gtagtgatat ccatattac  180 gcgagctggg cgaaaggccg attcaccatc tccaaaacct cgaccacggt ggatctgaaa 240
atcaccagtc cgacaaccga ggacacggcc acctatttct gtgccagaga tttaaatgct 300
ggttatttta tggtatatt ttatatttgg ggcccaggca ccctggtcac cgtctcttca  360
>A30633-VL
                                                    (SEQ ID NO: 5)
gagctcgtga tgacccagac tccatcctct gtgtctgcag ctgtgggagg cacagtcacc  60
atcacttgcc aggccagtca gagtcttagc aacctcttag cctggtatca gcagaaacca 120
gggcagcctc ccaagctcct gatctatggt gcatccaatc tggaatctgg ggtcccatcg 180
cgtttccgtg gcagtggatc tgggacagac ttcactctca ccatcagtgg catgaaggct 240
gaagatgctg ccacttatta ctgtcaaggt ggtcattata gtggtttgac ttttggaaat 300
ggcaccaatg tggaaatcaa a                                     321
>A30633-VH
                                                    (SEQ ID NO: 6)
cagtcgctgg aggagtccgg gggtcgcctg gtcacgcctg gacacccct gacactcacc   60 tgcacagtct ctggattctc cctcagtacc aacgacatga actgggtccg ccaggctcca 120
gggaaggggc tggaatggat cggagtcatt tatagtgatg ataccccccga ctacgcgacc 180 tgggcgaaag gccgattcac catctccaga acctcgacca cggtggatct gaaaatcacc 240
agtccgacaa ccgaggacac ggccacctat ttctgtgcca gaggtcatta cgacagtgct 300
gtttatgctt atgcccttaa catctggggc caggcaccc tggtcaccgt ctcttca    357
>A30514-VL
                                                    (SEQ ID NO: 7)
ELVMTQTPSS VSAAVGDTVT INCQASETVA TLLAWYQQKP GQPPKLLIYG ASNLESGVPS  60

RFRGSGSGTE FTLTISGMKA EDAATYYCQY GYISTGSNTF GAGTNVEIK            109
                                                    (SEQ ID NO: 13)
A30514 CDR-L1: QASETVATLLA;
                                                    (SEQ ID NO: 14)
A30514 CDR-L2: GASNLES;
                                                    (SEQ ID NO: 15)
A30514 CDR-L3: QYGYISTGSNTF
>A30514-VH
                                                    (SEQ ID NO: 8)
QEQLVESGGR LVTPGTPLTL TCTASGFSLG SDFMSWVRQA PGKGLEWIGY IDPRSDIPYY  60

ASWAKGRFTI SKTSTTVDLK ITSPTTEDTA TYFCARDLNA GYFNGIFYIW GPGTLVTVSS 120
                                                    (SEQ ID NO: 16)
A30514 CDR-H1: SDFMS;
                                                    (SEQ ID NO: 17)
A30514 CDR-H2: YIDPRSDIPYYASWAKG;
                                                    (SEQ ID NO: 18)
A30514 CDR-H3: DLNAGYFNGIFYI
>A30523-VL
                                                    (SEQ ID NO: 9)
ELDMTQTPSS TSEPVGGTVT INCQASQTIS SYLSWYQQKP GHPPKLLIYD ASDLASGVPS  60

RFSGSRSGTQ FTLTISGVQC DDAATYYCLG VYDYRSDDGA AFGGGTELEI L         111
```

```
                                                    (SEQ ID NO: 19)
A30523 CDR-L1: QASQTISSYLS;

(SEQ ID NO: 20)
A30523 CDR-L2: DASDLAS;

(SEQ ID NO: 21)
A30523 CDR-L3: LGVYDYRSDDGAA

>A30523-VH
                                                    (SEQ ID NO: 10)
QEQLVESGGR LVTPGTPLTL TCTASGFSLG SDFMSWVRQA PGKGLEWIGY IDPRSDIPYY    60

ASWAKGRFTI SKTSTTVDLK ITSPTTEDTA TYFCARDLNA GYFNGIFYIW GPGTLVTVSS   120

(SEQ ID NO: 22)
A30523 CDR-H1: SDFMS;

(SEQ ID NO: 23)
A30523 CDR-H2: YIDPRSDIPYYASWAKG;

(SEQ ID NO: 24)
A30523 CDR-H3: DLNAGYFNGIFYI

>A30633-VL
                                                    (SEQ ID NO: 11)
ELVMTQTPSS VSAAVGGTVT ITCQASQSLS NLLAWYQQKP GQPPKLLIYG ASNLESGVPS    60

RFRGSGSGTD FTLTISGMKA EDAATYYCQG GHYSGLTFGN GTNVEIK                107

(SEQ ID NO: 25)
A30633 CDR-L1: QASQSLSNLLA;

(SEQ ID NO: 26)
A30633 CDR-L2: GASNLES;

(SEQ ID NO: 27)
A30633 CDR-L3: QGGHYSGLT

>A30633-VH
                                                    (SEQ ID NO: 12)
QSLEESGGRL VTPGTPLTLT CTVSGFSLST NDMNWVRQAP GKGLEWIGVI YSDDTPDYAT    60

WAKGRFTISR TSTTVDLKIT SPTTEDTATY FCARGHYDSA VYAYALNIWG PGTLVTVSS   119

(SEQ ID NO: 28)
A30633 CDR-H1: TNDMN;

(SEQ ID NO: 29)
A30633 CDR-H2: VIYSDDTPDYATWAKG;

(SEQ ID NO: 30)
A30633 CDR-H3: GHYDSAVYAYALNI
```

See also FIG. 11(a)-(c).

In an embodiment of the invention, the A30633 heavy chain immunoglobulin variable domain is linked to an IgE constant chain and comprises the amino acid sequence:

```
                                                    (SEQ ID NO: 31)
QSLEESGGRLVTPGTPLTLTCTVSGFSLSTNDMNWVRQAPGKGLEWIGVI

YSDDTPDYATWAKGRFTISRTSTTVDLKITSPTTEDTATYFCARGHYDSA

VYAYALNIWGPGTLVTVSSASTQSPSVFPLTRCCKNIPSNATSVTLGCLA

TGYFPEPVMVTWDTGSLNGTTMTLPATTLTLSGHYATISLLTVSGAWAKQ

MFTCRVAHTPSSTDWVDNKTFSVCSRDFTPPTVKILQSSCDGGGHEPPTI

QLLCLVSGYTPGTINITWLEDGQVMDVDLSTASTTQEGELASTQSELTLS

QKHWLSDRTYTCQVTYQGHTFEDSTKKCADSNPRGVSAYLSRPSPFDLFI

RKSPTITCLVVDLAPSKGTVNLTWSRASGKPVNHSTRKEEKQRNGTLTVT

STLPVGTRDWIEGETYQCRVTHPHLPRALMRSTTKTSGPRAAPEVYAFAT

PEWPGSRDKRTLACLIQNEMPEDISVQWLHNEVQLPDARHSTTQPRKTKG

SGFFVFSRLEVTRAEWEQKDEFICRAVHEAASPSQTVQRAVSVNPGK
```

In an embodiment of the invention, the A30633 heavy chain immunoglobulin variable domain and IgE constant domain is encoded by a polynucleotide that comprises the nucleotide sequence:

```
                                                    (SEQ ID NO: 32)
CAGAGCCTGGAAGAGAGCGGCGGCAGACTGGTGACCCCTGGCACACCCCT

CACCCTGACATGTACAGTGTCCGGCTTTAGCCTGAGCACCAACGACATGA

ATTGGGTGAGACAGGCCCCTGGCAAAGGACTCGAGTGGATCGGCGTGATT

TACAGCGACGACACACCCGACTACGCCACATGGGCCAAGGGAAGATTCAC

CATCAGCAGGACCAGCACCACCGTGGACCTGAAAATCACATCCCCTACCA

CCGAAGACACCGCCACCTACTTCTGCGCCAGGGGCCACTACGATAGCGCC
```

GTCTACGCCTACGCCCTCAATATTTGGGGCCCTGGCACACTGGTGACCGT

GAGCAGCGCCAGCACCCAAAGCCCCAGCGTGTTCCCCCTGACAAGGTGTT

GCAAGAACATCCCCAGCAACGCCACCAGCGTCACACTGGGATGCCTGGCC

ACCGGCTACTTCCCCGAACCCGTCATGGTGACCTGGGATACCGGCAGCCT

GAATGGCACCACAATGACCCTCCCCGCCACAACCCTGACACTGAGCGGCC

ACTACGCCACCATCAGCCTGCTGACCGTGTCCGGCGCCTGGGCCAAACAG

ATGTTCACCTGCAGAGTGGCCCACACCCCCAGCTCCACAGACTGGGTGGA

CAACAAGACCTTCAGCGTGTGCTCCAGGGACTTTACACCCCCTACCGTGA

AGATCCTGCAGTCCAGCTGTGATGGCGGCGGCCACTTCCCTCCTACCATT

CAGCTCCTGTGCCTGGTGAGCGGCTACACACCCGGCACCATCAACATCAC

CTGGCTGGAGGATGGACAGGTGATGGACGTGGACCTCAGCACAGCCTCCA

CCACACAGGAGGGAGAGCTGGCCAGCACCCAGTCCGAGCTCACCCTGAGC

CAGAAGCACTGGCTGTCCGACAGGACCTATACATGCCAGGTCACCTACCA

GGGCCACACCTTCGAGGACTCCACAAAGAAGTGCGCCGACAGCAATCCCA

GAGGCGTCTCCGCCTACCTGTCCAGGCCTAGCCCCTTCGATCTGTTCATC

AGGAAGAGCCCCACCATTACATGCCTGGTGGTGGACCTGGCCCCCTCCAA

GGGCACCGTGAACCTGACCTGGAGCAGAGCCAGCGGCAAGCCCGTCAACC

ACTCCACCAGAAAGGAGGAGAAGCAGAGAAACGGCACCCTGACAGTGACC

TCCACACTCCCTGTGGGAACCAGGGACTGGATCGAGGGCGAGACCTATCA

GTGCAGAGTCACCCATCCCCATCTGCCCAGAGCCCTGATGAGAAGCACCA

CCAAGACATCCGGCCCCAGAGCTGCTCCTGAGGTGTACGCCTTTGCTACC

CCTGAGTGGCCCGGCTCCAGGGATAAGAGGACCCTCGCTTGCCTGATCCA

GAACTTCATGCCCGAAGACATCAGCGTGCAGTGGCTGCACAACGAGGTGC

AGCTGCCTGACGCCAGGCACAGCACAACCCAGCCTAGGAAGACCAAAGGC

TCCGGCTTTTTCGTGTTCTCCAGGCTCGAGGTGACCAGGGCCGAGTGGGA

GCAGAAAGATGAGTTCATCTGCAGGGCCGTGCACGAAGCTGCTAGCCCTA

GCCAGACCGTGCAAAGGGCTGTGTCCGTCAACCCCGGCAAGTGA

In an embodiment of the invention, the A30633 light chain immunoglobulin variable domain is linked to a human kappa constant domain and comprises the amino acid sequence:

(SEQ ID NO: 33)
ELVMTQTPSSVSAAVGGTVTITCQASQSLSNLLAWYQQKPGQPPKLLIYG

ASNLESGVPSRFRGSGSGTDFTLTISGMKAEDAATYYCQGGHYSGLTEGN

GTNVEIKRTVAAPSVFIFPPSDEQLKSGTASVVCLLNNEYPREAKVQWKV

DNALQSGNSQESVTEQDSKDSTYSLSSTLTLSKADYEKHKVYACEVTHQG

LSSPVTKSFNRGEC

In an embodiment of the invention, the A30633 light chain immunoglobulin variable domain and kappa chain is encoded by a polynucleotide that comprises the nucleotide sequence:

(SEQ ID NO: 34)
GAGCTGGTGATGACCCAGACACCCTCCTCCGTGAGCGCTGCTGTGGGCGG

AACCGTGACCATCACCTGCCAAGCCAGCCAGTCCCTGTCCAACCTGCTGG

CCTGGTACCAGCAGAAGCCTGGCCAGCCCCCCAAACTGCTGATCTACGGC

GCCAGCAACCTGGAGAGCGGCGTGCCTAGCAGGTTCAGGGGAAGCGGCAG

CGGCACCGACTTCACCCTGACCATCAGCGGCATGAAGGCCGAGGATGCCG

CCACCTACTACTGTCAGGGCGGCCACTACAGCGGCCTGACCTTCGGCAAC

GGCACCAACGTCGAGATCAAGAGGACCGTGGCCGCTCCCAGCGTCTTTAT

TTTCCCCCCTTCCGACGAGCAACTGAAAAGCGGCACCGCCAGCGTGGTGT

GCCTGCTGAACAACTTCTACCCCAGGGAGGCCAAGGTGCAGTGGAAGGTG

GATAACGCCCTGCAAAGCGGCAATAGCCAGGAGAGCGTGACCGAGCAGGA

CTCCAAGGACAGCACCTACTCCCTGAGCTCCACACTGACACTGAGCAAGG

CCGACTACGAGAAGCACAAGGTGTATGCCTGCGAGGTGACCCACCAGGGC

CTGAGCTCCCCTGTGACCAAGAGCTTCAACAGAGGAGAGTGCTGA

In an embodiment of the invention, the IgE heavy chain constant domain comprises the amino acid sequence:

(SEQ ID NO: 35)
ASTQSPSVFPLTRCCKNIPSNATSVTLGCLATGYFPEPVMVTWDTGSLNG

TTMTLPATTLTLSGHYATISLLTVSGAWAKQMFTCRVAHTPSSTDWVDNK

TFSVCSRDETPPTVKILQSSCDGGGHFPPTIQLLCLVSGYTPGTINITWL

EDGQVMDVDLSTASTTQEGELASTQSELTLSQKHWLSDRTYTCQVTYQGH

TFEDSTKKCADSNPRGVSAYLSRPSPFDLFIRKSPTITCLVVDLAPSKGT

VNLTWSRASGKPVNHSTRKEEKQRNGTLTVTSTLPVGTRDWIEGETYQCR

VTHPHLPRALMRSTTKTSGPRAAPEVYAFATPEWPGSRDKRTLACLIQNF

MPEDISVQWLHNEVQLPDARHSTTQPRKTKGSGFFVFSRLEVTRAEWEQK

DEFICRAVHEAASPSQTVQRAVSVNPGK

An antibody or antigen-binding fragment thereof that binds to pembrolizumab and comprises a light and heavy chain that includes the light and heavy chain CDRs marked A30514, A30523 or A30633 above may be referred to herein as "A30514", "A30523" or "A30633", respectively. "A30514", "A30523" or "A30633" antibodies and antigen-binding fragments may include one or more CDRs or light chains or heavy chains that are variants of those set forth above.

A "variant" of a polypeptide, such as an immunoglobulin chain, refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

In addition, a variant may be a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), non-sense mutations, deletions, or insertions. Such a polypeptide may be an immunoglobulin light chain, an immunoglobulin heavy chain and/or a CDR (e.g., any one or more of CDR-L1, CDR-L2, CDR-L3, CDR-H1, CDR-H2 and/or CDR-H3).

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3. "M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

The anti-pembrolizumab or antigen-binding fragments thereof of the present invention (e.g., humanized antibodies such as antagonist humanized antibodies) can comprise one, two, three, four, five, or six of the complementarity determining regions (CDRs) of the immunoglobulin chains disclosed herein (wherein 1, 2, 3, 4, 5 or 6 of the CDRs are, optionally, variants of those set forth herein). The one, two, three, four, five, or six CDRs may be independently selected from the CDR sequences of the various immunoglobulin chains disclosed herein. Alternatively, the one, two, three, four, five, or six CDRs may be selected from the CDR sequences of a single described antibody of the invention.

For example, the present invention includes anti-pembrolizumab antibodies and antigen-binding fragments thereof as well as immunoglobulin polypeptide chains wherein the antibody or antigen-binding fragment thereof or polypeptide chain comprises one or two of any of:
  the A30514 CDR-L1, CDR-L2 and CDR-L3;
  the A30514 CDR-H1, CDR-H2 and CDR-H3;
  the A30523 CDR-L1, CDR-L2 and CDR-L3;
  the A30523 CDR-H1, CDR-H2 and CDR-H3;
  the A30633 CDR-L1, CDR-L2 and CDR-L3; and
  the A30633 CDR-H1, CDR-H2 and CDR-H3.
e.g., wherein such antibodies are chimeric antibodies wherein the variable domains are fused to human IgE immunoglobulin heavy constant domain and/or a kappa light chain constant domain.

The anti-pembrolizumab antibodies or antigen-binding fragments thereof of the present invention can comprise at least one antibody heavy chain variable ($V_H$) domain comprising one or more (e.g., 3) of CDR-H1, CDR-H2 or CDR-H3 of A30514 $V_H$ (e.g., SEQ ID NO: 8); e.g., wherein the CDRs comprise the amino acid sequences set forth in SEQ ID NOs: 16 (or a variant thereof having 1, 2, 3, 4, 5, 6, 7, 8, 9 or 10 point mutations and/or point deletions), 17 (or a variant thereof having 1, 2, 3, 4, 5, 6, 7, 8, 9 or 10 point mutations and/or point deletions), and 18 (or a variant thereof having 1, 2, 3, 4, 5, 6, 7, 8, 9 or 10 point mutations and/or point deletions), respectively.

The anti-pembrolizumab antibodies or antigen-binding fragments thereof of the present invention can comprise at least one antibody light chain variable ($V_L$) domain comprising one or more (e.g., 3) of CDR-L1, CDR-L2 and CDR-L3 of the A30514 $V_L$ (e.g., SEQ ID NO: 7); e.g., wherein the CDRs comprise the amino acid sequences set forth in SEQ ID NOs: 13 (or a variant thereof having 1, 2, 3, 4, 5, 6, 7, 8, 9 or 10 point mutations and/or point deletions), 14 (or a variant thereof having 1, 2, 3, 4, 5, 6, 7, 8, 9 or 10 point mutations and/or point deletions) and 15 (or a variant thereof having 1, 2, 3, 4, 5, 6, 7, 8, 9 or 10 point mutations and/or point deletions), respectively.

The anti-pembrolizumab antibodies or antigen-binding fragments thereof of the present invention can comprise at least one antibody heavy chain variable ($V_H$) domain comprising one or more (e.g., 3) of CDR-H1, CDR-H2 or CDR-H3 of A30523 $V_H$ (e.g., SEQ ID NO: 10); e.g., wherein the CDRs comprise the amino acid sequences set forth in SEQ ID NOs: 22 (or a variant thereof having 1, 2, 3, 4, 5, 6, 7, 8, 9 or 10 point mutations and/or point deletions), 23 (or a variant thereof having 1, 2, 3, 4, 5, 6, 7, 8, 9 or 10 point mutations and/or point deletions), and 24 (or a variant thereof having 1, 2, 3, 4, 5, 6, 7, 8, 9 or 10 point mutations and/or point deletions), respectively.

The anti-pembrolizumab antibodies or antigen-binding fragments thereof of the present invention can comprise at least one antibody light chain variable ($V_L$) domain comprising one or more (e.g., 3) of CDR-L1, CDR-L2 and CDR-L3 of the A30523 $V_L$ (e.g., SEQ ID NO: 9); e.g., wherein the CDRs comprise the amino acid sequences set forth in SEQ ID NOs: 19 (or a variant thereof having 1, 2, 3, 4, 5, 6, 7, 8, 9 or 10 point mutations and/or point deletions), 20 (or a variant thereof having 1, 2, 3, 4, 5, 6, 7, 8, 9 or 10 point mutations and/or point deletions) and 21 (or a variant thereof having 1, 2, 3, 4, 5, 6, 7, 8, 9 or 10 point mutations and/or point deletions), respectively.

The anti-pembrolizumab antibodies or antigen-binding fragments thereof of the present invention can comprise at least one antibody heavy chain variable ($V_H$) domain comprising one or more (e.g., 3) of CDR-H1, CDR-H2 and CDR-H3 of A30633 $V_H$ (e.g., SEQ ID NO: 12); e.g., wherein the CDRs comprise the amino acid sequences set forth in SEQ ID NOs: 28 (or a variant thereof having 1, 2, 3, 4, 5, 6, 7, 8, 9 or 10 point mutations and/or point deletions), 29 (or a variant thereof having 1, 2, 3, 4, 5, 6, 7, 8, 9 or 10 point mutations and/or point deletions), and 30 (or a variant thereof having 1, 2, 3, 4, 5, 6, 7, 8, 9 or 10 point mutations and/or point deletions), respectively.

The anti-pembrolizumab antibodies or antigen-binding fragments thereof of the present invention can comprise at least one antibody light chain variable ($V_L$) domain comprising one or more (e.g., 3) of CDR-L1, CDR-L2 and CDR-L3 of the A30633 $V_L$ (e.g., SEQ ID NO: 11); e.g., wherein the CDRs comprise the amino acid sequences set forth in SEQ ID NOs: 25 (or a variant thereof having 1, 2, 3, 4, 5, 6, 7, 8, 9 or 10 point mutations and/or point deletions), 26 (or a variant thereof having 1, 2, 3, 4, 5, 6, 7, 8, 9 or 10 point mutations and/or point deletions) and 27 (or a variant thereof having 1, 2, 3, 4, 5, 6, 7, 8, 9 or 10 point mutations and/or point deletions), respectively.

The present invention provides an anti-pembrolizumab antibody or antigen-binding fragment thereof wherein the antibody or antigen-binding fragment thereof comprises:
 the A30514 CDR-H1, CDR-H2 and CDR-H3; and the A30514 CDR-L1, CDR-L2 and CDR-L3;
 the A30523 CDR-H1, CDR-H2 and CDR-H3; and the A30523 CDR-L1, CDR-L2 and CDR-L3; or
 the A30633 CDR-H1, CDR-H2 and CDR-H3; and the A30633 CDR-L1, CDR-L2 and CDR-L3;
e.g., wherein such antibodies are chimeric antibodies wherein the variable domains are fused to human IgE immunoglobulin heavy constant domain and/or a kappa light chain constant domain.

The present invention provides an anti-pembrolizumab antibody or antigen-binding fragment thereof wherein the antibody or antigen-binding fragment thereof comprises an antibody light chain variable ($V_L$) domain comprising a CDR-L1, CDR-L2 and CDR-L3 of the A30514 $V_L$ (e.g., SEQ ID NOs: 13 (or a variant thereof having 1, 2, 3, 4, 5, 6, 7, 8, 9 or 10 point mutations and/or point deletions), 14 (or a variant thereof having 1, 2, 3, 4, 5, 6, 7, 8, 9 or 10 point mutations and/or point deletions) and 15 (or a variant thereof having 1, 2, 3, 4, 5, 6, 7, 8, 9 or 10 point mutations and/or point deletions)); and an antibody heavy chain variable ($V_H$) domain comprising a CDR-H1, CDR-H2 and CDR-H3 of the A30514 $V_H$ (e.g., SEQ ID NOs: 16 (or a variant thereof having 1, 2, 3, 4, 5, 6, 7, 8, 9 or 10 point mutations and/or point deletions), 17 (or a variant thereof having 1, 2, 3, 4, 5, 6, 7, 8, 9 or 10 point mutations and/or point deletions) and 18 (or a variant thereof having 1, 2, 3, 4, 5, 6, 7, 8, 9 or 10 point mutations and/or point deletions)).

The present invention provides an anti-pembrolizumab antibody or antigen-binding fragment thereof wherein the antibody or antigen-binding fragment thereof comprises an antibody light chain variable ($V_L$) domain comprising a CDR-L1, CDR-L2 and CDR-L3 of the A30523 $V_L$ (e.g., SEQ ID NOs: 19 (or a variant thereof having 1, 2, 3, 4, 5, 6, 7, 8, 9 or 10 point mutations and/or point deletions), 20 (or a variant thereof having 1, 2, 3, 4, 5, 6, 7, 8, 9 or 10 point mutations and/or point deletions) and 21 (or a variant thereof having 1, 2, 3, 4, 5, 6, 7, 8, 9 or 10 point mutations and/or point deletions)); and an antibody heavy chain variable ($V_H$) domain comprising a CDR-H1, CDR-H2 and CDR-H3 of the A30523 $V_H$ (e.g., SEQ ID NOs: 22 (or a variant thereof having 1, 2, 3, 4, 5, 6, 7, 8, 9 or 10 point mutations and/or point deletions), 23 (or a variant thereof having 1, 2, 3, 4, 5, 6, 7, 8, 9 or 10 point mutations and/or point deletions) and 24 (or a variant thereof having 1, 2, 3, 4, 5, 6, 7, 8, 9 or 10 point mutations and/or point deletions)).

The present invention provides an anti-pembrolizumab antibody or antigen-binding fragment thereof wherein the antibody or antigen-binding fragment thereof comprises an antibody light chain variable ($V_L$) domain comprising a CDR-L1, CDR-L2 and CDR-L3 of the A30633 $V_L$ (e.g., SEQ ID NOs: 25 (or a variant thereof having 1, 2, 3, 4, 5, 6, 7, 8, 9 or 10 point mutations and/or point deletions), 26 (or a variant thereof having 1, 2, 3, 4, 5, 6, 7, 8, 9 or 10 point mutations and/or point deletions) and 27 (or a variant thereof having 1, 2, 3, 4, 5, 6, 7, 8, 9 or 10 point mutations and/or point deletions)); and an antibody heavy chain variable ($V_H$) domain comprising a CDR-H1, CDR-H2 and CDR-H3 of the A30633 $V_H$ (e.g., SEQ ID NOs: 28 (or a variant thereof having 1, 2, 3, 4, 5, 6, 7, 8, 9 or 10 point mutations and/or point deletions), 29 (or a variant thereof having 1, 2, 3, 4, 5, 6, 7, 8, 9 or 10 point mutations and/or point deletions) and 30 (or a variant thereof having 1, 2, 3, 4, 5, 6, 7, 8, 9 or 10 point mutations and/or point deletions)).

In a further embodiment, the antibody is a humanized anti-pembrolizumab antibody (e.g., IgE/kappa). Examples of such humanized anti-pembrolizumab antibodies include, but are not limited to, those comprising CDR-L1, CDR-L2 and CDR-L3 of A30514; and CDR-H1, CDR-H2 and CDR-H3 of A30514.

In a further embodiment, the antibody is a humanized anti-pembrolizumab antibody (e.g., IgE/kappa). Examples of such humanized anti-pembrolizumab antibodies include, but are not limited to, those comprising CDR-L1, CDR-L2 and CDR-L3 of A30523; and CDR-H1, CDR-H2 and CDR-H3 of A30523.

In a further embodiment, the antibody is a humanized anti-pembrolizumab antibody (e.g., IgE/kappa). Examples of such humanized anti-pembrolizumab antibodies include, but are not limited to, those comprising CDR-L1, CDR-L2 and CDR-L3 of A30633; and CDR-H1, CDR-H2 and CDR-H3 of A30633. In an embodiment of the invention, a A30633 humanized IgE/kappa antibody comprises the light and heavy chain sequences set forth in SEQ ID NOs: 33 and 31, respectively.

The present invention provides an anti-pembrolizumab antibody or antigen-binding fragment thereof or an immunoglobulin polypeptide wherein the antibody or antigen-binding fragment thereof or polypeptide comprises:
 the mature A30514 $V_L$ immunoglobulin domain and/or the mature A30514 $V_H$ domain;
 the mature A30523 $V_L$ immunoglobulin domain and/or the mature A30523 $V_H$ domain; or
 the mature A30633 $V_L$ immunoglobulin domain and/or the mature A30633 $V_H$ domain; e.g., wherein such antibodies are chimeric antibodies wherein the variable domains are fused to human IgE immunoglobulin heavy constant domain and/or a kappa light chain constant domain.

The present invention further provides an anti-pembrolizumab antibody or antigen-binding fragment thereof that comprises the mature $V_L$ domain of A30514, A30523 or A30633 wherein the $V_L$ domain comprises the amino acid sequence of SEQ ID NO: 7, 9 or 11, respectively, or a variant thereof.

The present invention further provides an anti-pembrolizumab antibody or antigen-binding fragment thereof that comprises the mature $V_H$ domain of A30514, A30523 or A30633 wherein the $V_H$ domain comprises the amino acid sequence of SEQ ID NO: 8, 10 or 12, respectively, or a variant thereof.

The present invention further provides an anti-pembrolizumab antibody or antigen-binding fragment thereof that comprises the mature $V_L$ domain of A30514 (e.g., SEQ ID NO: 7 or a variant thereof) and the mature $V_H$ domain of A30514 (e.g., SEQ ID NO: 8 or a variant thereof).

The present invention further provides an anti-pembrolizumab antibody or antigen-binding fragment thereof that comprises the mature $V_L$ domain of A30523 (e.g., SEQ ID NO: 9 or a variant thereof) and the mature $V_H$ domain of A30523 (e.g., SEQ ID NO: 10 or a variant thereof).

The present invention further provides an anti-pembrolizumab antibody or antigen-binding fragment thereof that comprises the mature $V_L$ domain of A30633 (e.g., SEQ ID NO: 11 or a variant thereof) and the mature $V_H$ domain of A30633 (e.g., SEQ ID NO: 12 or a variant thereof).

The invention also provides polypeptides comprising the amino acid sequence set forth in SEQ ID NO: 7 or a variant thereof; or any polynucleotide encoding such a polypeptide.

The invention also provides polypeptides comprising the amino acid sequence set forth in SEQ ID NO: 8 or a variant thereof; or any polynucleotide encoding such a polypeptide.

The invention also provides polypeptides comprising the amino acid sequence set forth in SEQ ID NO: 9 or a variant thereof; or any polynucleotide encoding such a polypeptide.

The invention also provides polypeptides comprising the amino acid sequence set forth in SEQ ID NO: 10 or a variant thereof; or any polynucleotide encoding such a polypeptide.

The invention also provides polypeptides comprising the amino acid sequence set forth in SEQ ID NO: 11 or a variant thereof; or any polynucleotide encoding such a polypeptide.

The invention also provides polypeptides comprising the amino acid sequence set forth in SEQ ID NO: 12 or a variant thereof; or any polynucleotide encoding such a polypeptide.

Single immunoglobulin chain polypeptides (e.g., any of SEQ ID NOs: 1-12) and polynucleotides that encode such polypeptides are useful, for example, as intermediates for the generation of antibodies such as A30514, A30523 or A30633.

The present invention includes crystalline compositions of the anti-pembrolizumab antibodies and antigen-binding fragments thereof of the present invention (e.g., A30514, A30523 or A30633).

The present invention provides antibodies that cross-block binding of the antibodies set forth herein (e.g., A30514, A30523 or A30633) from binding to pembrolizumab. The cross-blocking antibodies and antigen-binding fragments thereof discussed herein can be identified based on their ability to block any of the antibodies or fragments specifically set forth herein (e.g., A30514, A30523 or A30633), from binding to pembrolizumab in binding assays (e.g., bio-layer interferometry (BLI; for example FORTEBIO OCTET binding assay; Pall ForteBio Corp; Menlo Park, Calif.), surface plasmon resonance (SPR), BIACore, ELISA, flow cytometry). For example, in an embodiment of the invention, when using BLI, the tip of a fiber-optic probe is coated with ligand (e.g., pembrolizumab) and acts as the biosensor wherein binding of anti-pembrolizumab antibody or antigen-binding fragment to the pembrolizumab alters the interference pattern of white light reflected from the probe layer bound to pembrolizumab and an internal reference layer. The shift is indicative of pembrolizumab/anti-pembrolizumab binding. In an embodiment of the invention, the pembrolizumab coated tip is immersed in a solution of analyte containing antibody or antigen-binding fragment, e.g., in the well of either a 96- or 384-well plate. In an embodiment of the invention, the plate is shaken during reading to create orbital flow. To read the assay, white light is directed down the length of the fiber. As mentioned above, interference between light reflecting off the reference layer and immobilized surfaces containing pembrolizumab of the tip creates a distinctive pattern of light returning up the fiber. As molecules bind to the immobilized sensor surface, that pattern changes in proportion to the extent of binding. For example, assays can be used in which pembrolizumab is immobilized on a BLI probe or plate, a reference anti-pembrolizumab antibody or fragment binds to pembrolizumab (e.g., at saturating concentration) and a test anti-pembrolizumab antibody or fragment is added. The ability of the test antibody to compete with the reference antibody for pembrolizumab binding is then determined. In the BLI format, light interference of the pembrolizumab complex is monitored to determine if the test antibody effectively competes with the reference antibody, e.g., nanometers of light wavelength shift over time is monitored wherein a shift indicates additional binding of the test antibody and a lack of cross-blocking. In an embodiment of the invention, in the BLI format, cross-blocking is qualitatively deemed to have occurred between the antibodies if no additional binding of test antibody is observed. In an embodiment of the invention, as a control, cross-blocking of the reference antibody with itself is confirmed; wherein the assay is determined to be operating correctly if the reference antibody can cross-block itself from pembrolizumab binding. The ability of a test antibody to inhibit the binding of, for example, A30633, to pembrolizumab demonstrates that the test antibody can cross-block A30633 for binding to pembrolizumab and thus, may, in some cases, bind to the same epitope on pembrolizumab as A30633. As stated above, antibodies and fragments that bind to the same epitope as any of the anti-pembrolizumab antibodies or fragments of the present invention also form part of the present invention. In an embodiment of the invention, BLI is conducted in a sandwich format wherein a reference anti-pembrolizumab antibody or antigen-binding fragment is immobilized to the probe and then bound with pembrolizumab. Test anti-pembrolizumab antibody or antigen-binding fragment is then tested for the ability to block binding of the references antibody or fragment.

The present invention includes anti-pembrolizumab Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

The present invention includes anti-pembrolizumab antibodies and antigen-binding fragments thereof which comprise an Fc region and methods of use thereof. In an embodiment of the invention, an Fc is an IgE containing $C\epsilon1$, $C\epsilon2$, $C\epsilon3$ and $C\epsilon4$ domains. In an embodiment of the invention, an Fc is an IgG (e.g., IgG1, IgG2, IgG3 or IgG4) that contains $C_H1$ $C_H2$ and $C_H3$ domains. The two heavy chain fragments are held together by two or more disulfide bonds and by hydrophobic interactions of the $C_H3$ domains. In an embodiment of the invention, the antibody or fragment comprises a lambda or kappa light chain constant domain.

The present invention includes anti-pembrolizumab Fab' fragments and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule. The present invention also includes IgE Fab' and F(ab')$_2$ fragments. See Garman et al. Nature 406: 259-266 (2000) regarding the structure of IgE Fab fragments.

The present invention includes anti-pembrolizumab F(ab')$_2$ fragments and methods of use thereof. A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The present invention includes anti-pembrolizumab Fv fragments and methods of use thereof. The "Fv region" comprises the variable regions from both the heavy and light chains, but lacks the constant regions.

The present invention includes anti-pembrolizumab scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO88/01649 and U.S. Pat. Nos. 4,946,778 and 5,260,203.

The present invention includes anti-pembrolizumab domain antibodies and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The present invention includes anti-pembrolizumab bivalent antibodies and methods of use thereof. A "bivalent antibody" comprises two antigen-binding sites. In some instances, the two binding sites have the same antigen specificities. However, bivalent antibodies may be bispecific (see below).

The present invention includes anti-pembrolizumab nanobodies or single-domain antibodies. For example, anti-pembrolizumab antibodies of the present invention may be modified so as to prevent dimerization or aggregation such that nanobodies or single-domain antibodies are produced.

The present invention includes anti-pembrolizumab diabodies and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, an antibody or antigen-binding fragment of the invention which is modified in some way retains at least 10% of its pembrolizumab-binding activity (when compared to the parental antibody) when that activity is expressed on a molar basis. Preferably, an antibody or antigen-binding fragment of the invention retains at least 20%, 50%, 70%, 80%, 90%, 95% or 100% or more of the pembrolizumab binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes monoclonal anti-pembrolizumab antibodies and antigen-binding fragments thereof as well as monoclonal compositions comprising a plurality of isolated monoclonal antibodies. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) J. Mol. Biol. 222: 581-597, for example. See also Presta (2005) *J. Allergy Clin. Immunol.* 116:731.

The present invention includes anti-pembrolizumab chimeric antibodies (e.g., human constant domain/mouse variable domain) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) *Proc. Natl. Acad. Sci. USA* 81: 6851-6855). Typically, the variable domains are obtained from an antibody from an experimental animal (the "parental antibody"), such as a rodent or a rabbit, and the constant domain sequences are obtained from human antibodies (e.g., immunoglobulin E constant domain), so that the resulting chimeric antibody will be less likely to elicit an adverse immune response in a human subject than the parental (e.g., rabbit) antibody. Thus, the present invention includes anti-pembrolizumab antibodies and antigen-binding fragments thereof comprising a rabbit heavy and light chain variable domain of A30514, A30523 or A30633 linked to a human constant domain. In an embodiment of the invention, the human heavy chain constant domain is an IgE.

The present invention includes anti-pembrolizumab humanized antibodies and antigen-binding fragments thereof (e.g., mouse antibodies that have been humanized) and methods of use thereof. As used herein, the term "humanized antibody" refers to forms of antibodies that contain sequences from both human and non-human (e.g., rabbit) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

In an embodiment of the invention, anti-pembrolizumab antibodies of the present invention comprise a full tetrameric structure having two light chains and two heavy chains, including constant regions.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; a NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. CDR-L1, CDR-L2 and CDR-L3 in the light chain variable domain and CDR-H1, CDR-H2 and CDR-H3 in the heavy chain variable domain). See Kabat et al. (1991) Sequences of Proteins of Immunological Interest, 5th Ed. Public Health Service, National Institutes of Health, Bethesda, Md.; Johnson et al. (2001) Nucleic Acids Res. 2001; 29(1): 205-206 (defining the CDR regions of an antibody by sequence); see also Chothia and Lesk (1987) *J. Mol. Biol.* 196: 901-917; Chothia et al. Nature 342, 877 (1989), and Tramontano et al. J. Mol. Biol. 215, 175 (1990) (defining the CDR regions of an antibody by structure); see also Macallum et al. J Mol Biol. 1996 Oct. 11; 262(5):732-45. As used herein, the term "framework" or "FR" residues refers to those variable domain residues other than the hypervariable region residues defined herein as CDR residues.

As is discussed herein, the scope of the present invention includes anti-pembrolizumab antibodies and antigen-binding fragments thereof that bind pembrolizumab, which have CDRs from the immunoglobulin light chains of SEQ ID NOs: 7, 9 or 11 and/or which have CDRs from the immunoglobulin heavy chains of SEQ ID NOs: 8, 10 or 12. Such CDRs may be defined according to Kabat or Chothia (discussed herein).

Nucleic acids and polynucleotides encoding the immunoglobulins discussed herein (e.g., DNA or RNA) are not associated with all or a portion of a polynucleotide in which the isolated polynucleotide is found in nature, or is linked to a polynucleotide to which it is not linked in nature. For example, for purposes of this disclosure, it should be understood that "a polynucleotide comprising" a particular nucleotide sequence does not encompass intact chromosomes. Isolated polynucleotide "comprising" specified nucleotide sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences. As is discussed below, the present invention includes isolated polynucleotides encoding any of the immunoglobulin chains discussed herein.

The phrase "control sequences" refers to DNA sequences necessary or useful for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking may be accomplished by ligation at convenient restriction sites. If such sites do not exist, the synthetic oligonucleotide adaptors or linkers are used in accordance with conventional practice.

As used herein, the expressions "cell" and "cell line" and include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

Polynucleotides

The present invention further comprises the polynucleotides encoding any of the polypeptides or immunoglobulin chains of anti-pembrolizumab antibodies and antigen-binding fragments thereof disclosed herein (including variants of the amino acid chains specifically set forth herein). For example, the present invention includes the polynucleotides described in SEQ ID NOs: 1-6, 32 and 34; and variants thereof (e.g., comprising nucleotide sequences having at least 70%, 80%, 90%, 95% or 99% BLAST sequence identity to such nucleotide sequences (as discussed above). The scope of the present invention also includes variant polynucleotides that hybridize to any of such polynucleotides.

The present invention provides polynucleotides encoding the:
A30514 $V_L$ or a fragment thereof;
A30514 $V_H$ or a fragment thereof;
A30523 $V_L$ or a fragment thereof;
A30523 $V_H$ or a fragment thereof;
A30633 $V_L$ or a fragment thereof (or a A30633 $V_L$ fused to a kappa constant domain); and/or
A30633 $V_H$ or a fragment thereof (or a A30633 $V_H$ fused to an IgE constant domain).

The invention also provides polynucleotide comprising the nucleotide sequence set forth in SEQ ID NO: 1; or a variant thereof.

The invention also provides polynucleotide comprising the nucleotide sequence set forth in SEQ ID NO: 2; or a variant thereof.

The invention also provides polynucleotide comprising the nucleotide sequence set forth in SEQ ID NO: 3; or a variant thereof.

The invention also provides polynucleotide comprising the nucleotide sequence set forth in SEQ ID NO: 4; or a variant thereof.

The invention also provides polynucleotide comprising the nucleotide sequence set forth in SEQ ID NO: 5; or a variant thereof.

The invention also provides polynucleotide comprising the nucleotide sequence set forth in SEQ ID NO: 6; or a variant thereof.

The invention also provides polynucleotide comprising the nucleotide sequence set forth in SEQ ID NO: 32; or a variant thereof.

The invention also provides polynucleotide comprising the nucleotide sequence set forth in SEQ ID NO: 34; or a variant thereof.

Variant polynucleotides set forth herein include those that hybridize under low, moderate or high stringency conditions to the polynucleotides set forth herein or to polynucleotides that encode the polypeptides set forth herein, and encode immunoglobulin chains of anti-pembrolizumab antibodies or antigen-binding fragments thereof which maintain the ability to bind to pembrolizumab. A first polynucleotide molecule is "hybridizable" to a second polynucleotide molecule when a single stranded form of the first polynucleotide molecule can anneal to the second polynucleotide molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two polynucleotide contain complementary sequences, although, depending on the stringency of the hybridization, mismatches between bases are possible. The appropriate stringency for hybridizing polynucleotides depends on the length of the polynucleotides and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter polynucleotides, e.g., oligonucleotides, the position of mismatches becomes more important, and the length of the oligonucleotide determines its specificity (see Sambrook, et al., supra, 11.7-11.8).

In another embodiment of the invention, a polynucleotide, for example DNA, encoding the immunoglobulin polypeptide chains of the anti-pembrolizumab antibodies or antigen-binding fragments set forth herein forms part of the present invention. In one embodiment of the invention, the polynucleotide encodes at least one mature immunoglobulin polypeptide light chain variable ($V_L$) domain and at least one mature immunoglobulin polypeptide heavy chain variable ($V_H$) domain, wherein the $V_L$ domain comprises a CDR-L1, CDR-L2 and CDR-L3 having a sequence selected from SEQ ID NOs: 13-15, 19-21 and 25-27, and the $V_H$ domain comprises CDR-H1, CDR-H2 and CDR-H3 having a sequence selected from SEQ ID NOs: 16-18, 22-24 and 28-30. In one embodiment of the invention, the polynucleotide encodes the A30514, A30523, A30633 mature light chain variable region and/or the A30514, A30523, A30633 mature heavy chain variable region sequences. In some embodiments of the invention, the polynucleotide encodes both a light chain and a heavy chain on a single polynucleotide molecule, and, in other embodiments of the invention, the light and heavy chains are encoded on separate polynucleotide molecules, e.g., in separate or common host cells. In another embodiment of the invention, the polynucleotides further encode a signal sequence.

In one embodiment of the invention, the polynucleotide encodes a mature immunoglobulin light chain variable ($V_L$) domain comprising the CDR-L1, CDR-L2 and CDR-L3 of SEQ ID NO: 7. Variants of such polynucleotides are also part of the present invention.

In one embodiment of the invention, the polynucleotide encodes a mature immunoglobulin heavy chain variable ($V_H$) domain comprising the CDR-H1, CDR-H2 and CDR-H3 of SEQ ID NO: 8. Variants of such polynucleotides are also part of the present invention.

In one embodiment of the invention, the polynucleotide encodes a mature immunoglobulin light chain variable ($V_L$) domain comprising the CDR-L1, CDR-L2 and CDR-L3 of SEQ ID NO: 9. Variants of such polynucleotides are also part of the present invention.

In one embodiment of the invention, the polynucleotide encodes a mature immunoglobulin heavy chain variable ($V_H$) domain comprising the CDR-H1, CDR-H2 and CDR-H3 of SEQ ID NO: 10. Variants of such polynucleotides are also part of the present invention.

In one embodiment of the invention, the polynucleotide encodes a mature immunoglobulin light chain variable ($V_L$) domain comprising the CDR-L1, CDR-L2 and CDR-L3 of SEQ ID NO: 11. Variants of such polynucleotides are also part of the present invention.

In one embodiment of the invention, the polynucleotide encodes a mature immunoglobulin heavy chain variable ($V_H$) domain comprising the CDR-H1, CDR-H2 and CDR-H3 of SEQ ID NO: 12. Variants of such polynucleotides are also part of the present invention.

This present invention also provides vectors, e.g., expression vectors, such as plasmids, comprising the polynucleotides of the invention (sequences set forth herein and variants thereof, e.g., SEQ ID NO: 32 and/or 34), wherein the polynucleotide is operably linked to control sequences that are recognized by a host cell when the host cell is transfected with the vector. Also provided are host cells comprising a polynucleotide (e.g., integrated into the genome, e.g., a chromosome, of the host cell) or vector of the present invention and methods for producing the antibody or antigen-binding fragment thereof or polypeptide disclosed herein.

Methods for Making

The present invention includes methods for making an anti-pembrolizumab antibody or antigen-binding fragment thereof of the present invention, or an immunoglobulin chain thereof, comprising (i) introducing a polynucleotide encoding one or more immunoglobulin chains of the antibody or fragment (e.g., SEQ ID NOs: 7-12, 31 and/or 33 or any of those discussed herein), for example, wherein the polynucleotide is in a vector and/or is operably linked to a promoter; (ii) culturing the host cell (e.g., CHO or *Pichia* or *Pichia pastoris*) under condition favorable to expression of the polynucleotide and, (iii) optionally, isolating the antibody or fragment or chain from the host cell and/or medium in which the host cell is grown. When making an antibody or antigen-binding fragment comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antibody or antigen-binding fragment molecule. The methods include those wherein only a heavy immunoglobulin chain is expressed or only a light immunoglobulin chain is expressed or both heavy and light chains are expressed (e.g., any of those discussed herein including mature fragments and/or variable domains thereof). In embodiments wherein heavy and light immunoglobulin chains are expressed, the chains can be expressed from two separate polynucleotide molecules or from a single polynucleotide molecule.

Single unpaired immunoglobulin chains are useful, for example, as intermediates in the expression of an antibody or antigen-binding fragment that includes such a chain.

Anti-pembrolizumab antibodies can also be synthesized by any of the methods set forth in U.S. Pat. No. 6,331,415.

Eukaryotic and prokaryotic host cells, including mammalian cells as hosts for expression of the anti-pembrolizumab antibodies or fragments or immunoglobulin chains disclosed herein, are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Host cells also include those which have been selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharomyces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp., *Yarrowia lipolytica*, and *Neurospora crassa*.

Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell. The present invention includes methods for purifying an anti-pembrolizumab antibody or antigen-binding fragment thereof of the present invention comprising introducing a sample (e.g., culture medium, cell lysate or cell lysate fraction, e.g., a soluble fraction of the lysate) comprising the antibody or fragment to a purification medium (e.g., cation-exchange medium, anion-exchange medium, hydrophobic exchange medium, affinity purification medium (e.g., protein-A, protein-G, protein-A/C, protein-L)) and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium; or wherein the antibody or fragment is secreted into the culture medium by the host cell and the medium or a fraction thereof is applied to the purification medium.

Antibody Conjugates

The anti-pembrolizumab antibodies (e.g., humanized antibodies such as antagonist humanized antibodies) and antigen-binding fragments thereof disclosed herein (e.g., A30514, A30523 or A30633) may also be conjugated to a chemical moiety. Such conjugated antibodies and fragments are part of the present invention. The chemical moiety may be, inter alia, a polymer or a radionuclide. In particular embodiments, the chemical moiety is a polymer. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The anti-pembrolizumab antibodies (e.g., humanized antibodies such as antagonist humanized antibodies) and antigen-binding fragments thereof disclosed herein (e.g., A30514, A30523 or A30633) may also be conjugated with labels (e.g., detectable labels such as radiolabels) such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{216}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe. In an embodiment of the invention, the antibody or fragment is labeled with ruthenium (and, optionally, in the presence of tripropylamine).

The anti-pembrolizumab antibodies and antigen-binding fragments disclosed herein (e.g., A30514, A30523 or A30633) may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the anti-pembrolizumab antibodies and antigen-binding fragments thereof (e.g., A30514, A30523 or A30633) to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies and fragments are conventional and very well known in the art.

Assays

The present invention provides methods for using the anti-pembrolizumab antibodies and antigen-binding fragments thereof to determine the presence of anti-drug antibodies (ADAs) in a sample. For example, the anti-pembrolizumab antibodies and antigen-binding fragments thereof can be used as positive controls in assays for ADAs.

The present invention provides a method for generating an pembrolizumab/anti-pembrolizumab antibody or antigen-binding fragment thereof complex comprising the step of contacting pembrolizumab and anti-pembrolizumab antibody or antigen-binding fragment thereof under conditions wherein each may associate and form a complex. In an embodiment of the invention, the complex is additionally bound to a secondary antibody that binds to the anti-pembrolizumab antibody or fragment. Such compositions form part of the present invention. In an embodiment of the invention, the pembrolizumab is immobilized to a solid substrate such as the wall of a microtiter plate (e.g., plastic or glass). The present invention includes anti-pembrolizumab antibody or antigen-binding fragments thereof that are immobilized to a solid substrate (e.g., glass or plastic or polysaccharide).

The present invention comprises a positive-control assay that comprises:
(1) contacting pembrolizumab antibody that is immobilized to a support with an anti-pembrolizumab antibody or antigen-binding fragment thereof of the present invention;
(2) contacting the anti-pembrolizumab antibody or fragment with a labeled secondary antibody; and
(3) determining the presence of label immobilized to the support;
wherein the presence of the label immobilized to the support indicates that the pembrolizumab is bound to the anti-pembrolizumab antibody or antigen-binding fragment thereof of the present invention.

In an embodiment of the invention, the pembrolizumab is biotinylated and is bound to streptavidin on the support. In an embodiment of the invention, the anti-pembrolizumab is ruthenylated; wherein the presence of the anti-pembrolizumab antibody or fragment is detected by contacting the ruthenium with tripropylamine (TPA) or another co-reactant for light generation by the ruthenium and determination of light output from the pembrolizumab/anti-pembrolizumab complex.

The present invention provides a method for determining the presence of ADAs in a sample comprising:
a first assay that comprises:
(i) contacting pembrolizumab antibody that is immobilized to a support with a sample to be tested for the presence of ADAs under conditions wherein a complex between the pembrolizumab and ADAs can form (and, optionally, washing unbound antibodies and ADAs away);
  (ii) contacting any ADAs in the sample that are bound to the pembrolizumab with a labeled secondary antibody (and, optionally, washing away unbound secondary antibodies); and
  (iii) determining the presence of immobilized label;
wherein the presence of the label immobilized to the support in the first assay indicates the presence of ADAs in the sample; and a second assay which is a positive-control assay the comprises:
  (a) contacting pembrolizumab antibody that is immobilized to a support with an anti-pembrolizumab antibody or antigen-binding fragment thereof of the present invention under conditions wherein a complex between the pembrolizumab and anti-pembrolizumab antibodies or fragments can form (and, optionally, washing unbound antibodies or fragments away), e.g., wherein the anti-pembrolizumab antibody or fragment is detectably labeled, e.g., with ruthenium;
  (b) optionally, contacting the anti-pembrolizumab antibody or fragment with a labeled secondary antibody (and, optionally, washing away unbound secondary antibodies); and
  (c) determining the presence of immobilized label;
wherein the presence of the label immobilized to the support in the second assay indicates that the assay is functioning correctly. In an embodiment of the invention, the immobilized label is ruthenium which emits a detectable signal when developed, for example, with a reagent such as TPA.

In an embodiment of the invention, the sample to be tested for the presence of ADAs can take any form including blood, serum or plasma or a composition derived therefrom, e.g., of a patient who had been administered pembrolizumab.

The secondary antibody that is detectably labeled can be, for example, an anti-IgE antibody if the anti-pembrolizumab antibody or antigen-binding fragment thereof of the present invention is an IgE. In an embodiment of the invention, the secondary antibody is labeled with a radiolabel (e.g., $^{131}I$, $^{32}P$, $^{3}H$, $^{35}S$), an enzyme (e.g., horseradish peroxidase or acid phosphatase), a substrate (e.g., biotin) or a fluorescent compound (e.g., Alexa Fluor® 405, AMCA (Aminomethylcoumarin), Cy2 (cyanine), DyLight® 488, Alexa Fluor® 488, FITC, Alexa Fluor® 555, Cy3 (Indocarbocyanine), Phycoerythrin, TRITC, DyLight® 550, Rhodamine, TAMRA, Cy3.5, Alexa Fluor® 568, PE/Texas Red®, Texas Red®, Alexa Fluor® 594, DyLight® 594, APC, Cy5 (Indodicarbocyanine), Alexa Fluor® 647, PE/Cy7, DyLight® 650, Cy5.5, PE/Cy5.5, Alexa Fluor® 680, Alexa Fluor® 750, APC/Cy7 or Alexa Fluor® 790).

The present invention also provides a method for identifying an agent that binds to PD1 based on whether the agent competes with an anti-pembrolizumab antibody or antigen-binding fragment thereof. For example, in an embodiment of the invention, the method comprises contacting a PD1 polypeptide or fragment thereof with the agent in the presence of the anti-pembrolizumab antibody or fragment. If the agent competes with the anti-pembrolizumab antibody or fragment for binding to the PD1, then the agent is determined to bind to PD1. In an embodiment of the invention, the anti-pembrolizumab antibody or fragment is detectably labeled (e.g., radiolabeled) and the agent is not labeled, e.g., wherein binding of the labeled antibody or fragment to PD1 is monitored and a decrease in binding of the labeled antibody or fragment indicates that the agent is competing for binding to PD1.

EXAMPLES

These examples are intended to exemplify the present invention are not a limitation thereof. Compositions and methods set forth in the Examples form part of the present invention.

Example 1: Generation of Anti-Pembrolizumab Antibody (1) Project Overview
An anti-pembrolizumab idiotypic human IgE chimeric antibody was developed by phage display method. The following steps were carried out:
Step 1: Animal immunization;
Step 2: Phage display library construction;
Step 3: Phage display panning;
Step 4: Lead antibody screening and affinity ranking;
Step 5: Chimeric antibody construction and production.
(2) Materials
Pembrolizumab IgG4 antibody
Active human IgG4 full length protein (Abcam, Cat. No.: ab90286)
ELISA microtiter plates (Corning, Cat. No.: 9018)
Coating buffer: 0.05 M $NaHCO_3$, pH 9.6
PBS: 137 mM NaCl, 2.7 mM KCl, 10 mM $Na_2HPO_4$, 2.0 mM $KH_2PO_4$, pH 7.4
Blocking buffer (PBST): PBS buffer, pH 7.4, with 5% skimmed milk
Washing buffer: PBS buffer, pH 7.4, with 0.05% Tween 20
Goat anti-rabbit IgG [HRP] (GenScript, Cat. No.: A00098)
TRIzol Reagent (Ambion, Cat. No.: 15596-026)
PrimeScript™ 1st Strand cDNA Synthesis Kit (Takara, Cat. No.: 6110A)
Sfi I enzyme (NEB, Cat. No.: R0123S)
BsiW I enzyme (NEB, Cat. No.: R0553L)
Nhe I enzyme (NEB, Cat. No.: R0131S)
Nco I enzyme (NEB, Cat. No.: R3193S)
Host strain: *E. coli* TG1
M13KO7 helper phage (NEB, Cat. No.: NO3155)
HRP/Anti-M13 monoclonal antibody (GE Healthcare, Cat. No.: 27-9421-01)
2×YT: 1.6% Tryptone, 1.0% Yeast extract, 0.5% NaCl, pH7.4
Ampicillin (100 mg/ml)
Kanamycin (30 mg/ml)
PEG/NaCl: 20% PEG6000, 2.5 M NaCl
OctetRED96 (FortéBio)
Amine Reactive 2nd Generation (AR2G) Dip and Read™ Biosensors (FortéBio, Part No.: 18-5092)
BIAcore T200 (GE Healthcare)
Series S Sensor Chip CM5 (GE Healthcare, Cat. No.: BR-1005-30)
HBS-EP: 10 mM HEPES, 150 mM NaCl, 3 mM EDTA, 0.005% Tween 20, pH 7.4
PBST: 137 mM NaCl, 2.7 mM KCl, 10 mM $Na_2HPO_4$, 2.0 mM $KH_2PO_4$, 0.05% Tween 20, pH 7.4
10 mM Glycine-HCl, pH 2.0
37° C. $CO_2$ incubator (Thermo Scientific, Model. 3951)
Biological safety cabinet (Thermo Scientific, Model. 1384)
Orbital shaker (Thermo Scientific, Model. 416)
Polyethylenimine (Polysciences, Cat. No.: 23966)
FreeStyle 293 medium (Invitrogen Life Technologies, Cat. No.: 12338-018)
Tryptone N1 (Organotechnie, Cat. No.: 19553)
500-ml shake flask (Corning, Cat. No.: 421145)
Protein-L resin (GenScript, Cat. No.: L00239)

Binding buffer: 0.15 M NaCl, 20 mM $Na_2HPO_4$, pH 8.5
Elution buffer: 0.1 M Glycine-HCl, pH 2.5
Neutralization buffer: 1 M Tris-HCl, pH 9.0
PD-10 Desalting Column (GE Healthcare, Cat. No.: 17-0851-01)
Nanodrop 2000 (Thermo Scientific, Serial No.: D171)
(3) Methods
3.1 Animal Immunization An immunogen, pembrolizumab F(ab')$_2$ protein (henceforth called F(ab')$_2$ protein), was mixed with adjuvant and injected to two New Zealand white rabbits (New Zealand white rabbit ID 1985 and 1986, the schedule is listed in Table 1)).

TABLE 1

Schedule of immunization.

| Procedure | Schedule | Dosage/Route | Adjuvant |
|---|---|---|---|
| Pre-immune bleed | Day −4 | (3 ml blood taken) | |
| Initial immunization | Day 0 | 200 μg MK-XXXX F(ab')2/animal, s.c. | CFA |
| 1$^{st}$ boost | Day 14 | 200 μg MK-XXXX F(ab')2/animal, s.c. | IFA |
| Test bleed 1 | Day 21 | (6 ml blood taken) | |
| 2$^{nd}$ boost | Day 35 | 200 μg MK-XXXX F(ab')2/animal, s.c. | IFA |
| Test bleed 2 | Day 42 | (6 ml blood taken) | |
| 3$^{rd}$ boost | Day 56 | 200 μg MK-XXXX F(ab')2/animal, s.c. | IFA |
| Test bleed 3 | Day 63 | (6 ml blood taken) | |
| Exsanguinations and splenectomy | Day 64 | | |

Peripheral blood samples were collected at the pre-immunization stage and after each boost immunization. The immune response was evaluated by ELISA using the prepared serum samples. The F(ab')$_2$ protein was diluted in coating buffer at 4 μg/ml and coated the microtiter plate at 4° C. overnight. The plates were then washed with washing buffer for 3 times before being blocked with blocking buffer at 37° C. for 2 hours. The plates were washed again with washing buffer for 4 times. A series of diluted sera was added to the plates and incubated at 37° C. for 2 hours. Then, the plates were washed with washing buffer for 4 times. Goat anti-rabbit IgG [HRP] secondary antibody was added to the plate and incubated at 37° C. for 1 hour. After washing, the reaction was developed with TMB substrate for 10 minutes and stopped by 1 M HCl. The absorbance of each well at 450 nm was measured using MK3 spectrometer. PBMCs and splenocytes were isolated in the terminal bleeding step for phage display library construction 3.2 Phage Display Library Construction
3.2.1 RNA Extraction Total RNA was extracted from rabbit splenocytes and PBMCs (from 3.1). The quantity and quality of total RNA was measured by gel electrophoresis and OD 260/280.

3.2.2 Amplification of Rabbit VH and VL cDNA by RT-PCR

Total RNA was reverse transcribed into cDNA using oligo(dT)20 primer according to the manual of PrimeScript™ 1$^{st}$ Strand cDNA Synthesis Kit. Four forward and one reverse specific degenerate primers were designed for the amplification of VH fragments while three forward and three reverse specific degenerate primers were designed for the amplification of VL fragments.

3.2.3 Fab Phage Display Library Construction

The VH and VL PCR products were obtained by amplification using different primer pairs. The VH products were digested with Nco I/Nhe I and VL products were digested with Sfi I/BsiW I. The digested fragments were purified via gel electrophoresis and inserted into GenScript's in-house phagemid vector (FIG. 1). The VH was cloned into GenScript in-house phagemid with Nco I/Nhe I, firstly and a ~9.84×10$^7$ heavy chain library (insert rate 100%) was obtained. The VL fragment mixture was then cloned into the plasmid pool of heavy chain library with Sfi I/BsiW I and transformed into TG1 cells by electroporation. A pilot library was constructed to optimize the ligation and transformation condition. The optimized ligation and transformation condition was employed to develop the real library. A small portion of the transformed cells was diluted and streaked on 2×YT plates supplemented with 100 μg/ml ampicillin. The colonies were counted to calculate the library size. Positive clones were randomly picked and sequenced to assess the quality of the library. The rest of the transformed cells were streaked onto Ø15 cm 2×YT plates supplemented with 100 μg/ml ampicillin and 2% glucose. Lawns of colonies were scraped off the plates. A small aliquot of the cells were used for library plasmids isolation. The rest was supplemented with glycerol and stored at −80° C. as stock.

3.3 Phage Display Panning
3.3.1 Biopanning

The constructed Fab phage library was panned against F(ab')$_2$ protein. A Fab phage-display library containing 1.2× 10$^8$ clones (CFU) was used for the selection. The library stock was grown in log phase, then rescued with M13KO7 helper phage and amplified overnight in 2×YT containing 100 μg/ml ampicillin and 50 μg/ml kanamycin at 25° C. on a shaker. The phage was precipitated with PEG/NaCl, and was resuspended in PBS and store at −80° C.

For phage panning, phage particles were incubated with blocking buffer of PBS containing 2% skimmed milk and active human IgG4 full length protein at room temperature for 1 hour to block nonspecific binding. Then, phage particles were added to the F(ab')$_2$ antigen protein coated wells (or tubes) and were incubated on a shaker at room temperature for 1 hour. After incubation, unbound and nonspecifically bound phages were washed away by rinsing 8 times with PBST (PBS containing 0.05% Tween-20) and then another 2 times with PBS. The bound phage particles were then immediately eluted by 0.1 M TEA solution and used to infect exponentially growing E. coli TG1 cells (OD at 600 nm ~0.5) for 1 h at 37° C. After each round of panning, the infected cells were mixed with 10% glycerol and were then stored at −80° C. For the next round of panning, the infected E. coli TG1 cell stock was added to 30 ml of 2×YT containing 200 μg/ml ampicillin and 2% glucose medium and was grown to log phase. The culture was rescued with M13KO7 helper phage. The output page was amplified, precipitated, and used for the next round of selection. Regular phage display panning was repeated as described above.

3.3.2 Phage ELISA

Individual output phage clones were picked and grown in a 96-deep-well plate and screened by phage ELISA to identify the F(ab')$_2$ protein specific clones. ELISA microtiter plates were coated with 1 μg/ml F(ab')$_2$ protein and active human IgG4 full length protein overnight at 4° C., separately. The plates were blocked with blocking buffer. Approximately 50 μl per well of phage supernatant from the overnight TG1 cell culture was added to the plate and incubated at 4° C. for 2 hours. The plate was washed with washing buffer 4 times before incubation with HRP-conjugated anti-M13 monoclonal antibody at 4° C. for 1 hour. The wells were washed again with washing buffer 4 times. The TMB substrate solution was added to each well for color development. The absorption was measured at 450 nm. The positive phage binders were selected and sent for DNA sequencing to obtain the Fab DNA sequences.

3.4 Lead Antibody Screening and Affinity Ranking 3.4.1 FASEBA Screening

DNAs encoding Fab antibodies of the positive output phage were amplified and inserted into pFASEBA vector for screening of the lead antibodies. Individual FASEBA library clones were inoculated and induced for expression in 96-deep-well plates. ELISA screening was performed to selected Fab antibody which recognize F(ab')$_2$ protein specifically, and the positive clone culture medium were selected for affinity ranking by the BIAcore T200.

3.4.2 Affinity Ranking

BSA was immobilized onto the sensor chip using amine coupling method. Three Fab-SASA secreted to the culture medium were injected and captured by BSA via SASA (capture phase). After equilibration, antigen F(ab')$_2$ protein or active human IgG4 was injected for 300 seconds (association phase) followed by the injection of running buffer (dissociation phase). Responses of reference flow cell (flow cell 1) were subtracted from those of Fab-SASA flow cells during each cycle. The binding curves of Fab-SASA were aligned at the start of association and normalized at 20 seconds after analyte injection completion using the BIAcore T200 evaluation software to display a more visualized comparison of antibodies. The off-rates of Fab-SASA clones were obtained from fitting the experimental data locally to 1:1 binding model. The antibodies were ranked by their dissociation rate constants (off-rates, kd).

3.5 Chimeric Antibody Construction and Production 3.4.1 Chimeric Antibody Construction DNAs encoding selected Fab antibodies were amplified and inserted into pTT5 vector for human rabbit IgE chimeric antibodies production.

3.4.2 Pilot Expression and Purification

For transfection, 50 μg each of light chain and heavy chain expression plasmids were pre-mixed with 300 μl Polyethylenimine (PEI) stock solution (1 mg/ml) and 10 ml pre-warmed Freestyle 293 medium, then the mixture was incubated for 10 minutes at room temperature to allow complexes to form. The mixture was added into 90 ml of suspended HEK293-6E cells in Freestyle 293 medium at a cell density of approximately 2.0×10$^6$ cells per ml. The mixture was transferred into a 500-ml shaker flask, and incubated at 37° C. and 5% CO$_2$ on an orbital shaker rotating with constant shaking at 110 rpm. Pre-warmed TN1 was added into the cell culture with a final concentration of 0.5% (w/v) at 24 h post-transfection. The conditioned medium was harvested at 5-6 days post-transfection by centrifugation at 1500×g for 10 minutes to remove cells. The supernatants were used for the subsequent purification. The supernatants were passed through a 0.22 μm filter to remove cell debris. Protein-L resin was resuspended with binding buffer and the slurry was transferred to a fresh column filled with 1 ml binding buffer. Samples were loaded into an affinity column, followed by washing with 20 CV (column volumes) of binding buffer. The protein was eluted with elution buffer and immediately neutralized to ~pH 7.0 afterwards with neutralization buffer. The purified antibody was exchanged into PBS using PD-10 desalting column. The concentration and purity of the purified protein were determined by OD280 and SDS-PAGE, respectively.

3.4.3 Chimeric Sntibody Characterization

The binding between purified chimeric antibody and F(ab')$_2$ protein or active human IgG4 protein were validated using OctetRed 96. The assay was performed at 30° C. in 1× Kinetics assay buffer (1×PBS, 0.05% Tween-20, pH 7.4). Samples were agitated at 1000 rpm. Prior to analysis, AR2G sensors were humidified for 15 min. The purified chimeric antibody was coated on the sensor by amine coupling method. Three concentrations (50, 12.5 and 3.125 nM) of analyte (F(ab')$_2$ protein or active human IgG4 protein) were used. The association was monitored for 300 s and the dissociation was monitored for 600 s. The data was processed by GraphPad Prism 5.0 software.

3.4.4 Scale-up Production

For transfection, 500 μg each of light chain and heavy chain expression plasmids were pre-mixed with 3 ml Polyethylenimine (PEI) stock solution (1 mg/ml) and 10 ml pre-warmed Freestyle 293 medium, then the mixture was incubated for 10 minutes at room temperature to allow complexes to form. The mixture was added into 1 L of suspended HEK293-6E cells in Freestyle 293 medium at a cell density of approximately 2.0×10$^6$ cells per ml. The mixture was transferred into a 3 L shaker flask, and incubated at 37° C. and 5% CO$_2$ on an orbital shaker rotating with constant shaking at 110 rpm. Pre-warmed TN1 was added into the cell culture with a final concentration of 0.5% (w/v) at 24 h post-transfection. The conditioned medium was harvested at 5-6 days post-transfection and subsequent purification by centrifugation at 1500×g for 10 minutes to remove cells. For purification, the supernatants were passed through a 0.22 μm filter to remove cell debris and purified using Protein-L resin as mentioned before (3.4.2). The purified antibody was exchanged into PBS using PD-10 desalting column. The concentration and purity of the purified protein were determined by OD280 and SDS-PAGE, respectively.

(4) Results 4.1 Immune Response Test

Figure 2:
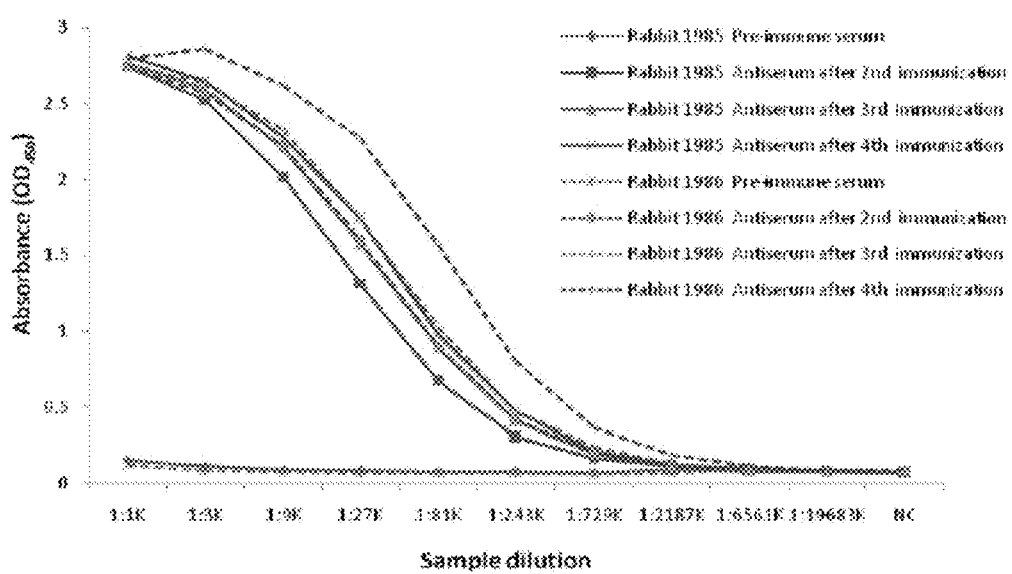
FIG. 2. Immune response evaluation for F(ab')$_2$ protein. NC: negative control.

The immune response evaluation results are shown in FIG. 2. The sera titers for the test bleeds were much higher than the pre-immune bleed. No significant difference was observed between different test bleed samples.

4.2 sdAb Phage Display Library Construction 4.2.1 Total RNA extraction

Figure 3:
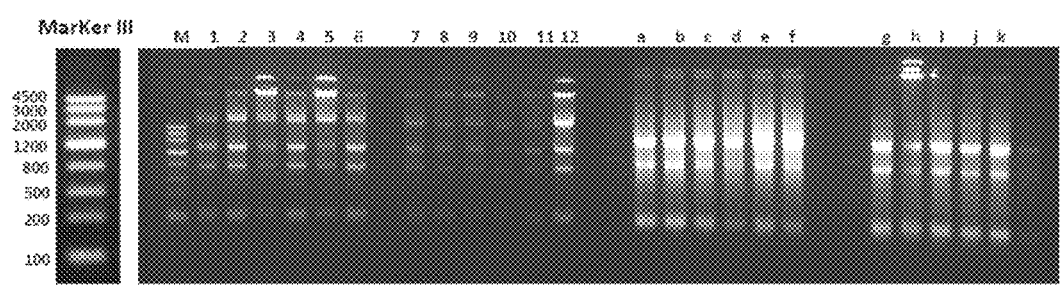
FIG. 3. Agarose gel electrophoresis of total obtained RNA. Lane M, DNA Marker III; Lane 1~6, total RNA isolated from PBMCs of ID 1985 rabbit; Lane 7~12, total RNA isolated from PBMCs of ID 1986 rabbit; Lane a~f, total RNA isolated from spleen of ID 1985 rabbit; Lane g~k, total RNA isolated from spleen of ID 1986 rabbit.

About 2.3 mg total RNA was obtained from PBMCs and spleen of two immunized rabbits with ID 1985 and ID 1986. (FIG. 3), and about 360 μg total RNA from PBMCs and spleen were used to construct the high-quality library.

4.2.2 RT-PCR and VH/L Amplification

Figure 4:
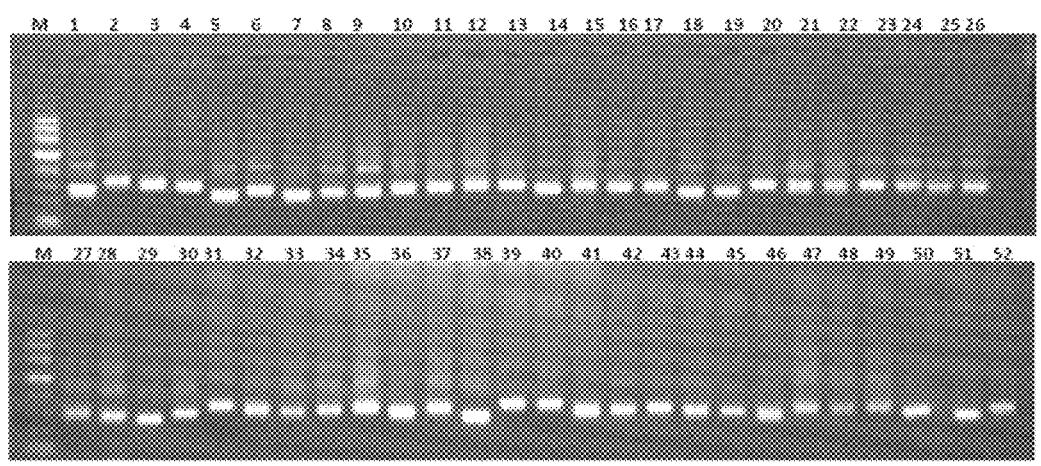
FIG. 4. Agarose gel electrophoresis of purified VH and VL PCR products. Lane M, DNA Marker III; Lane 1~4, Purified VH PCR products derived from PBMCs of ID 1985 rabbit using 4 primer pairs. Lane 5~13, Purified VL PCR products derived from PBMCs of ID 1985 rabbit using 9 primer pairs. Lane 14~17, Purified VH PCR products derived from PBMCs of ID 1986 rabbit using 4 primer pairs. Lane 18~26, Purified VL PCR products derived from PBMCs of ID 1986 rabbit using 9 primer pairs. Lane 27~30, Purified VH PCR products derived from splenocytes of ID 1985 rabbit using 4 primer pairs. Lane 31~39, Purified VL PCR products derived from splenocytes of ID 1986 rabbit using 9 primer pairs. Lane 40~43, Purified VH PCR products derived from splenocytes of ID 1986 rabbit using 4 primer pairs. Lane 44~52, Purified VL PCR products derived from splenocytes of ID 1986 rabbit using 9 primer pairs.

RT-PCR was performed using 4 pairs of primers for VH amplification and 9 pairs of primers for VL amplification according to GenScript's SOP. The products obtained using different primer pairs were combined and gel-purified (FIG. 4). About 20 μg pure VH PCR products and 50 μg VL PCR products were obtained. Half of the PCR products were used for library construction.

Figure 5:
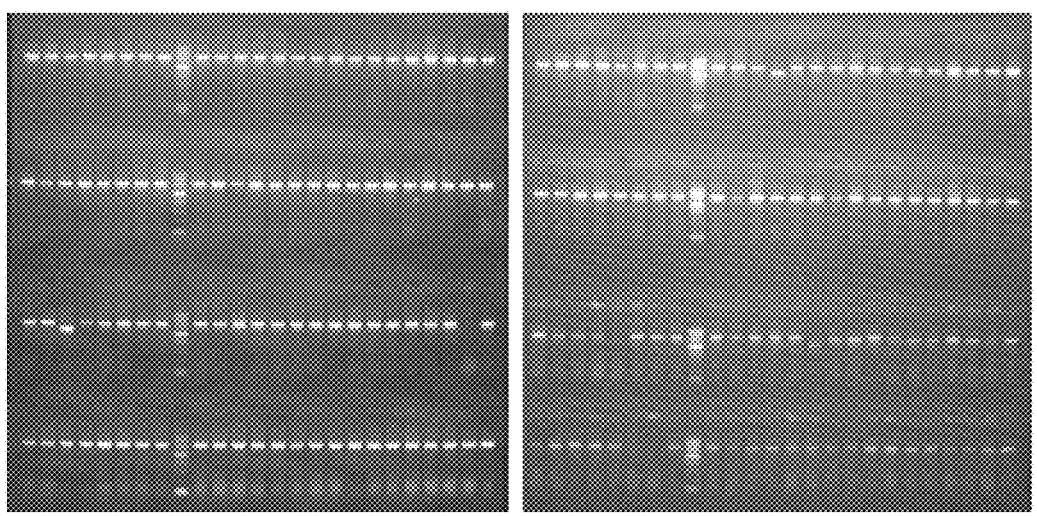
FIG. 5. Fab phage display library insert rate evaluation. 96 randomly picked clones of library were amplified by PCR using primers M13R (−48) and M13F (−47). Clones with ~2100 by DNA band have Fab fragment inserts.
Figure 6:
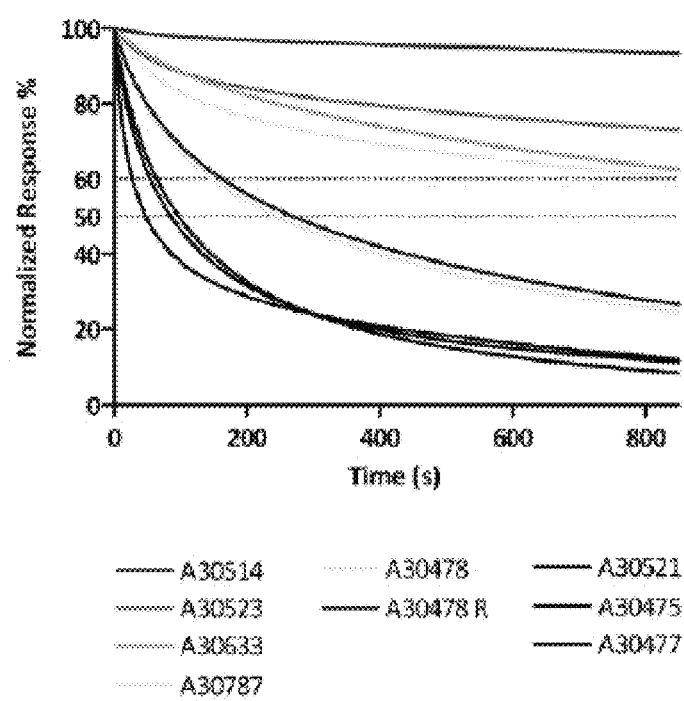
FIG. 6. Sensorgram of off-rate ranking of secreted Fab antibodies for F(ab')$_2$ protein. A30514, A30523 and A30633 were the top three high affinity binders.
Figure 7:
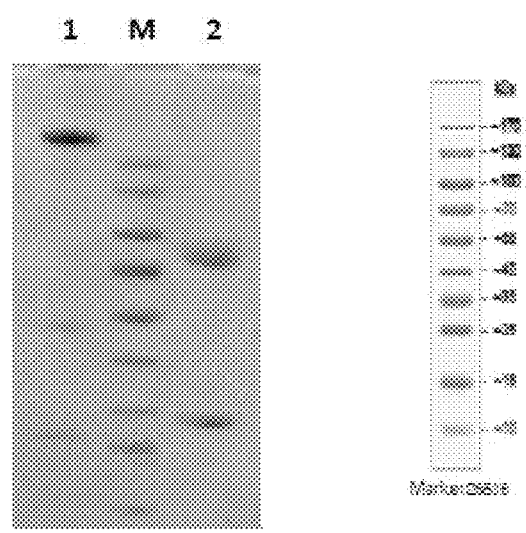
FIG. 7. SDS-PAGE analysis of purified A30633 human IgE chimeric antibody. Lane 1, 2 μg purified A30633 under non-reducing condition; Lane 2, 2 μg purified A30633 under reducing condition; Lane M, page ruler pre-stained protein ladder (Thermo Scientific, Cat. No.: 26616).
Figure 8:
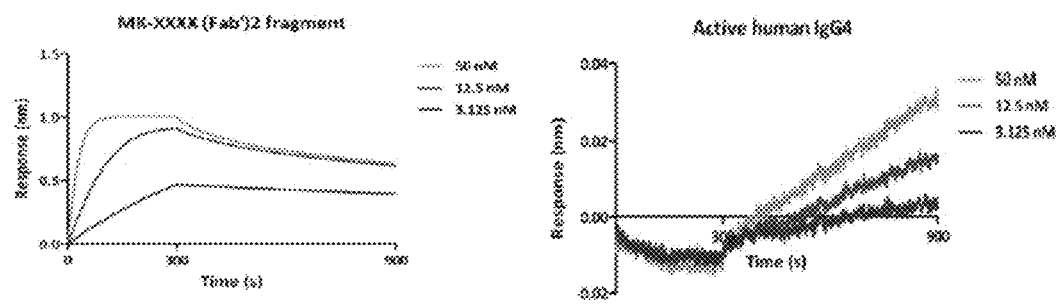
FIG. 8. Validation of the interaction between purified A30633 human IgE chimeric antibody and antigens. The purified A30633 was immobilized as ligand and the two antigens, F(ab')$_2$ protein and active human IgG4 protein, were used as analyte. Active human IgG4 was set as negative control.
Figure 9:
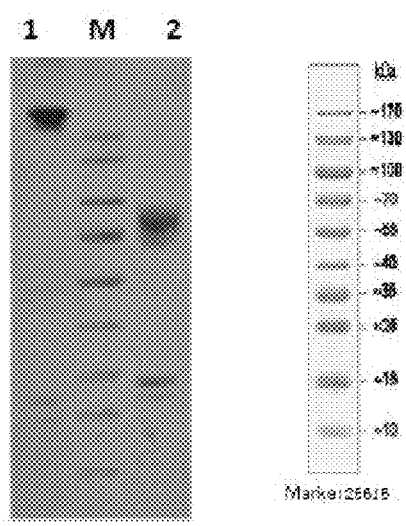
FIG. 9. SDS-PAGE analysis of purified A30633 human IgE chimeric antibody. Lane 1, 2 μg purified A30633 under non-reducing condition; Lane 2, 2 μg purified A30633 under reducing condition; Lane M, page ruler pre-stained protein ladder (Thermo Scientific, Cat. No.: 26616).
Figure 10:
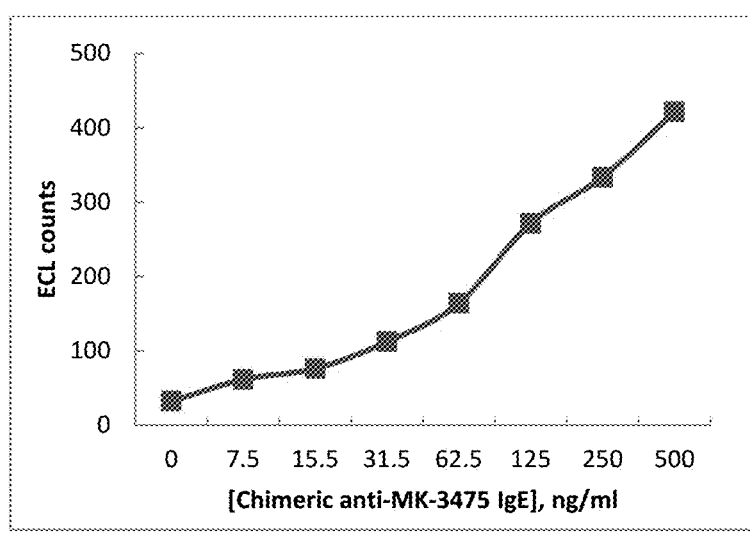
FIG. 10. ELISA data demonstrating binding of increasing concentrations of anti-pembrolizumab antibody to pembrolizumab.

According to the number of transformants, at least 3.5× 10$^6$ transformants were obtained from one set of electro-transformation, so 36 transformations were conducted in parallel to generate the final library. The library was estimated to be ~1.2×10$^8$. The insert rate was 95.8% (184/192) according to colony screening (FIG. 5).

4.2.4 Library Diversity Evaluation 105 clones with the right Fab fragment insert were sent for sequencing for in-frame rate and library diversity evaluation (Table 2). 19 clones are out of frame due to the amplification, the library in-frame rate is 81.9% (86/105). The remained 86 Fab sequences could be grouped into 86 groups (VL: 69 groups, VH: 85 groups). The amino acids alignment data were listed in Appendix I and Appendix II.

TABLE 2

Sequencing analysis of Fab phage display library.

| Total clones | In-frame rate | Fab Diversity (Groups) | Library diversity |
| --- | --- | --- | --- |
| 105 | 81.9% (86/105) | 86 | 100% (86/86) |

The binding of several identified antibodies was determined and the $k_{off}$ rates were calculated. These data are set forth below in Table 3.

TABLE 3

Dissociation rate ($k_{off}$) of indicated antibodies for binding to pembrolizumab

| Sample ID | $k_{off}$(1/s) |
| --- | --- |
| A30514 | 6.5E−05 |
| A30523 | 3.4E−04 |
| A30633 | 1.2E−03 |
| A30478 | 9.4E−02 |
| A30787 | 4.1E+01 |
| A30521 | 4.5E+01 |
| A30475 | 5.6E+01 |
| A30477 | 3.9E+04 |

(5) Conclusion 8 unique Fab clones were selected as lead antibodies against the pembrolizumab F(ab')$_2$ protein from phage panning and FASEBA screening. The A30633 Fab antibody was selected for human IgE chimeric antibody construction and production. The binding of purified A30633 human IgE chimeric antibody and pembrolizumab F(ab')$_2$ protein was confirmed by OctetRED96.

Example 2: ELISA Assay Using Chimeric Anti-Pembrolizumab IgE A30633 as the Positive Control The chimeric anti-pembrolizumab IgE was applied as the positive control for developing an anti-pembrolizumab antibodies of IgE isotype assay. In this assay, the biotinylated pembrolizumab was used as the capture and ruthenylated anti-human IgE was used as the detector. Initially, the biotinylated pembrolizumab at 100 ng/mL was added to a MesoScale Discovery (MSD) 96 well plate coated with streptavidin, and incubated for approximately an hour. After the removal of unbound Biotinylated pembrolizumab, the chimeric anti-pembrolizumab IgE at different concentrations were added to the wells, and allowed for overnight incubation at 4° C. On day 2, the wells were washed to remove the unbound samples, followed by the addition of ruthenylated anti-human IgE at 200 ng/mL. After an hour of incubation, the wells were washed, and 1× Read buffer was added before analyzed by MSD Sector Imager 6000 reader. Read Buffer is a Tris-based buffer containing tripropylamine (TPA) as a co-reactant for light generation in electrochemiluminescence immunoassays. The graph in FIG. 10 demonstrated that a dose response was observed as the concentration of the chimeric anti-pembrolizumab IgE increased. It suggests that the chimeric anti-pembrolizumab can serve as a positive control for the anti-drug antibody assay.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. An antibody or antigen-binding fragment thereof that binds pembrolizumab, comprising: three light chain CDRs of CDR-L1, CDR-L2 and CDR-L3 and three heavy chain CDRs of CDR-H1, CDR-H2 and CDR-H3, wherein
   CDR-L1 comprises the amino acid sequence: QASQSLSNLLA (SEQ ID NO: 25);
   CDR-L2 comprises the amino acid sequence: GASNLES (SEQ ID NO: 26);
   CDR-L3 comprises the amino acid sequence: QGGHYSGLT (SEQ ID NO: 27);
   CDR-H1 comprises the amino acid sequence: TNDMN (SEQ ID NO: 28);
   CDR-H2 comprises the amino acid sequence: VIYSDDTPDYATWAKG (SEQ ID NO: 29); and
   CDR-H3 comprises the amino acid sequence: GHYDSAVYAYALNI (SEQ ID NO: 30).

2. The antibody or antigen-binding fragment of claim 1 which comprises a light chain immunoglobulin and a heavy chain immunoglobulin, wherein:
   the light chain immunoglobulin comprises an amino acid sequence having at least 90% amino acid sequence identity to the amino acid sequence set forth in SEQ ID NO: 11; and the heavy chain immunoglobulin comprises an amino acid sequence having at least 90% amino acid sequence identity to the amino acid sequence set forth in SEQ ID NO: 12.

3. The antibody or antigen-binding fragment of claim 2 wherein said sequence identity is at least 95%.

4. The antibody or antigen-binding fragment of claim 1 comprising: a light chain immunoglobulin comprising the amino acid sequence set forth in SEQ ID NO: 11; and a heavy chain immunoglobulin comprising the amino acid sequence set forth in SEQ ID NO: 12.

5. The antibody of claim 1, which is a monoclonal antibody.

6. A composition comprising an anti-pembrolizumab antibody or antigen-binding fragment thereof of claim 1 complexed with pembrolizumab.

* * * * *